United States Patent
Fiddian-Greene et al.

(10) Patent No.: US 6,238,339 B1
(45) Date of Patent: May 29, 2001

(54) REMOTE SENSING TONOMETRIC CATHETER APPARATUS AND METHOD

(75) Inventors: Richard G. Fiddian-Greene, Boston, MA (US); Bo Holte, Charlottenlund (DK); Joel C. Kent, Needham, MA (US); Börje Tor Rantala, Helsinki (FI)

(73) Assignee: Instrumentarium Corp., Helsinki (FI)

(*) Notice: Subject to any disclaimer, the term of this patent is extended or adjusted under 35 U.S.C. 154(b) by 0 days.

(21) Appl. No.: 08/433,399

(22) PCT Filed: Mar. 18, 1994

(86) PCT No.: PCT/US94/03018

§ 371 Date: May 8, 1995

§ 102(e) Date: May 8, 1995

(87) PCT Pub. No.: WO94/21164

PCT Pub. Date: Sep. 29, 1994

Related U.S. Application Data

(63) Continuation-in-part of application No. 08/035,020, filed on Mar. 22, 1993, now abandoned, which is a continuation-in-part of application No. 08/014,624, filed on Feb. 8, 1993, now abandoned, and a continuation-in-part of application No. 07/719,097, filed on Jun. 20, 1991, now abandoned, and a continuation-in-part of application No. 07/994,721, filed on Dec. 22, 1992, now abandoned.

(51) Int. Cl.[7] ............................................. A61B 5/00
(52) U.S. Cl. ..................... 600/309; 600/504; 600/353
(58) Field of Search ................................ 128/632, 635, 128/673, 691, 736, 748, 749, 774, 778, 780, 782; 600/309–310, 322–327, 345–353, 363–366, 504–505

(56) References Cited

U.S. PATENT DOCUMENTS

| | | | |
|---|---|---|---|
| 3,983,864 | 10/1976 | Sielaff et al. | 128/230 |
| 4,221,567 | * 9/1980 | Clark et al. | 128/635 |
| 4,233,513 | 11/1980 | Elder et al. | 250/343 |
| 4,273,636 | 6/1981 | Shimada et al. | 204/195 |
| 4,423,739 | 1/1984 | Passaro et al. | 128/719 |
| 4,480,190 | 10/1984 | Burough et al. | 250/343 |
| 4,576,590 | 3/1986 | Fiddian-Green | 604/26 |
| 4,596,931 | 6/1986 | Ehnholm et al. | 250/343 |
| 4,643,192 | 2/1987 | Fiddian-Green | 128/632 |
| 4,671,287 | 6/1987 | Fiddian-Green | 128/631 |
| 4,677,143 | 6/1987 | Laurin et al. | 523/122 |
| 4,859,858 | 8/1989 | Knodle et al. | 250/504 |
| 4,859,859 | 8/1989 | Knodle et al. | 250/343 |
| 4,907,166 | 3/1990 | Corenman et al. | 364/497 |

(List continued on next page.)

FOREIGN PATENT DOCUMENTS

| | | |
|---|---|---|
| 340908 | 11/1989 | (EP) . |
| 92/10971 | 7/1992 | (WO) . |

OTHER PUBLICATIONS

Gastrotonometry—An Aid to the Control of Ventilation During Artificial Respiration, D. Boda, The Lancet, Jan. 24, 1959, pp. 181–182.

(List continued on next page.)

Primary Examiner—John P. Lacyk
(74) Attorney, Agent, or Firm—Andrus, Sceales, Starke & Sawall, LLP

(57) ABSTRACT

An improved remote sensing tonometric catheter apparatus (20) and method for sampling of a fluid or gas property of interest in a hollow internal organ. The tonometric catheter (20) assists in early detection of the problems of stress ulceration and/or intestinal ischemia. The tonometric catheter (20) can be one or more sampling chambers (40) for introduction into an internal organ or area adjacent thereto. Preferably, the wall (36) of the sampling chamber (40) is freely permeable to the gas or fluid to be measured by the sensor (42), but is poorly permeable to other gases or fluids which may interfere with the sensor (42).

98 Claims, 11 Drawing Sheets

U.S. PATENT DOCUMENTS

| | | | |
|---|---|---|---|
| 4,914,720 | 4/1990 | Knodle et al. | 250/343 |
| 5,042,522 | 8/1991 | Corenman et al. | 137/239 |
| 5,067,492 | 11/1991 | Yelderman et al. | 128/719 |
| 5,095,913 | 3/1992 | Yelderman et al. | 128/719 |
| 5,158,083 | 10/1992 | Sacristan et al. | 128/635 |
| 5,174,290 | 12/1992 | Fiddian-Green | 128/632 |
| 5,186,172 | 2/1993 | Fiddian-Green | 128/632 |
| 5,423,320 | 6/1995 | Salzman et al. | 128/664 |
| 5,479,923 | 1/1996 | Rantala. | |

OTHER PUBLICATIONS

Gastric Intramucosal pH as a Therapeutic Index of Tissue Oxygenation in Critically Ill Patients, G. Gutierrez, F. Palizas et al., The Lancet, vol. 339, Jan. 25, 1992, pp. 195–199.

Splanchnic Ischemia and Multiple Organ Failure, R. G. Fiddian–Green et al., C. V. Mosby Co., 1989, pp. 349–363.

Clinical Evaluation of a Raman Scattering Multiple Gas Analyzer for the Operating Room, D. R. Westenskow et al. Anesthesiology 70:350–355, 1989.

Raman Scattering for Respiratory Gas Monitoring in the Operating Room: Advantages, Specifications, and Future Advances, D. R. Westenskow et al., Biomedical Instrumentation & Technology, Nov./Dec. 1989, pp. 485–489.

Monitoring Anesthetic and Respiratory Gases, Daniel B. Raemer, James H. Philip, Monitoring in Anesthesia and Critical Care Medicine, pp. 373–386.

Air Tonometry: A New Method for Determination of Gastrointestinal Mucosal $pCO_2$, Critical Care Medicine, Andrew L. Salzman et al., pp. S202, Apr. 1993.

Noninvasive Carbon Dioxide Monitoring, M. Christine Stock, Critical Care Clinics, vol. 4, No. 3, Jul. 1988, pp. 511–526.

Multichannel Raman Spectroscopy Tackles Industrial Problems, T. M. Niemczyk et al., Laser Focus World, Mar. 1993, pp. 85–98.

\* cited by examiner

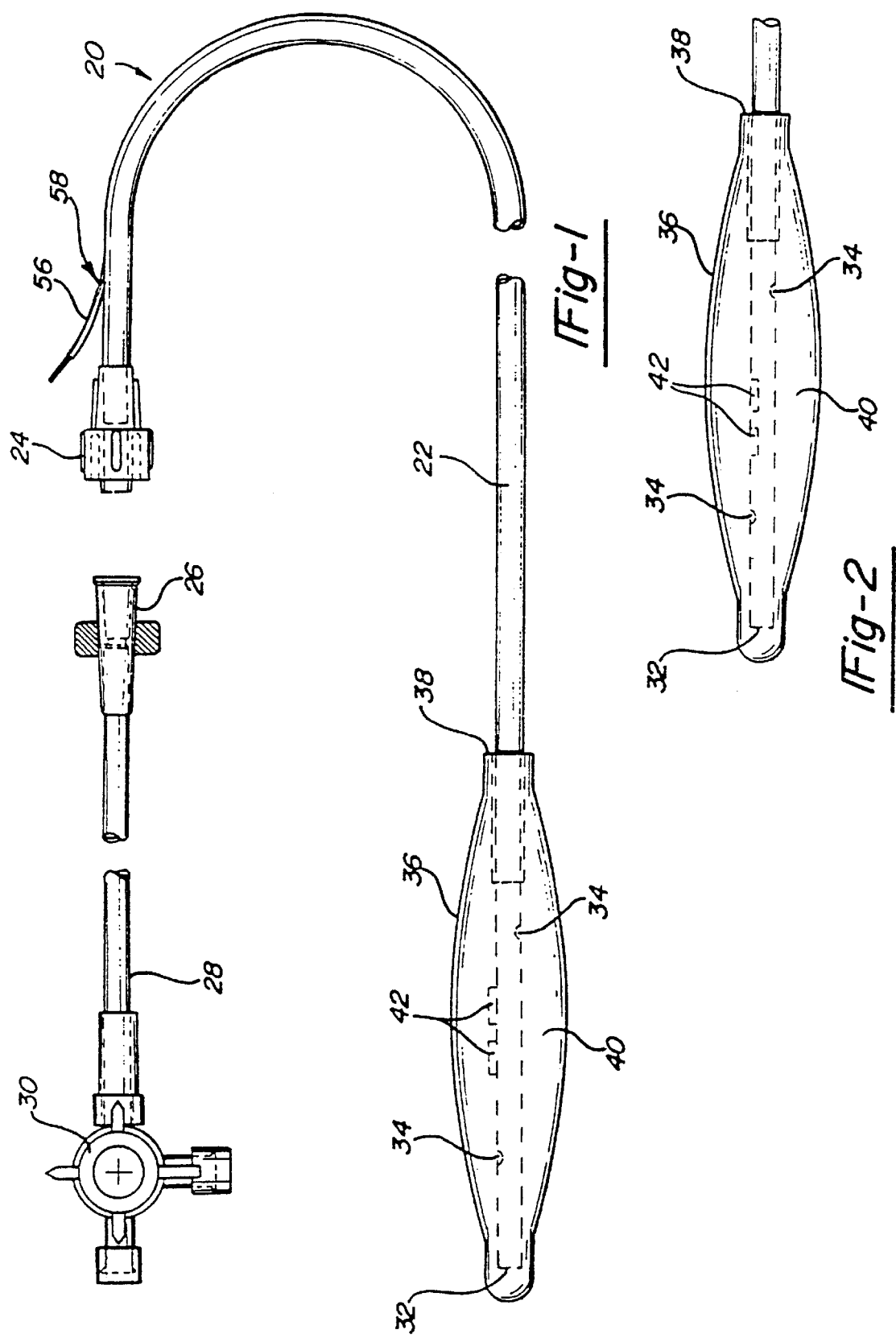

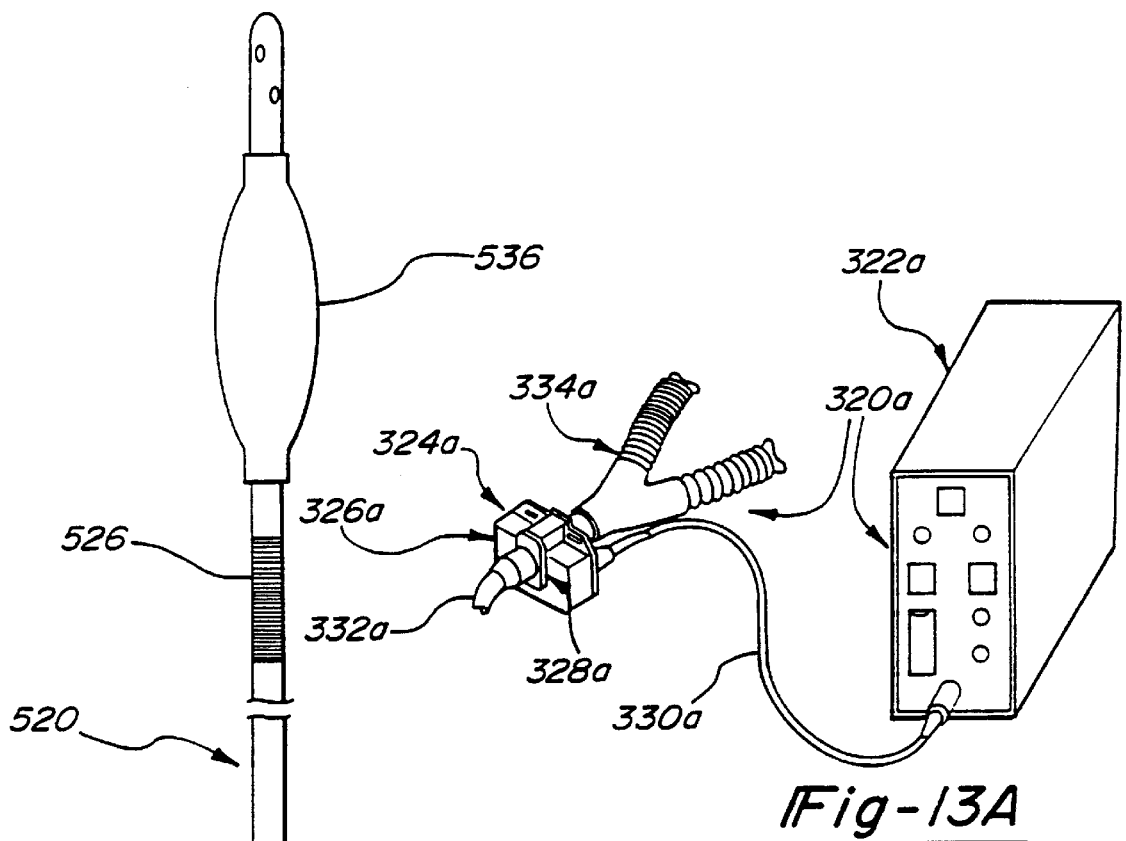
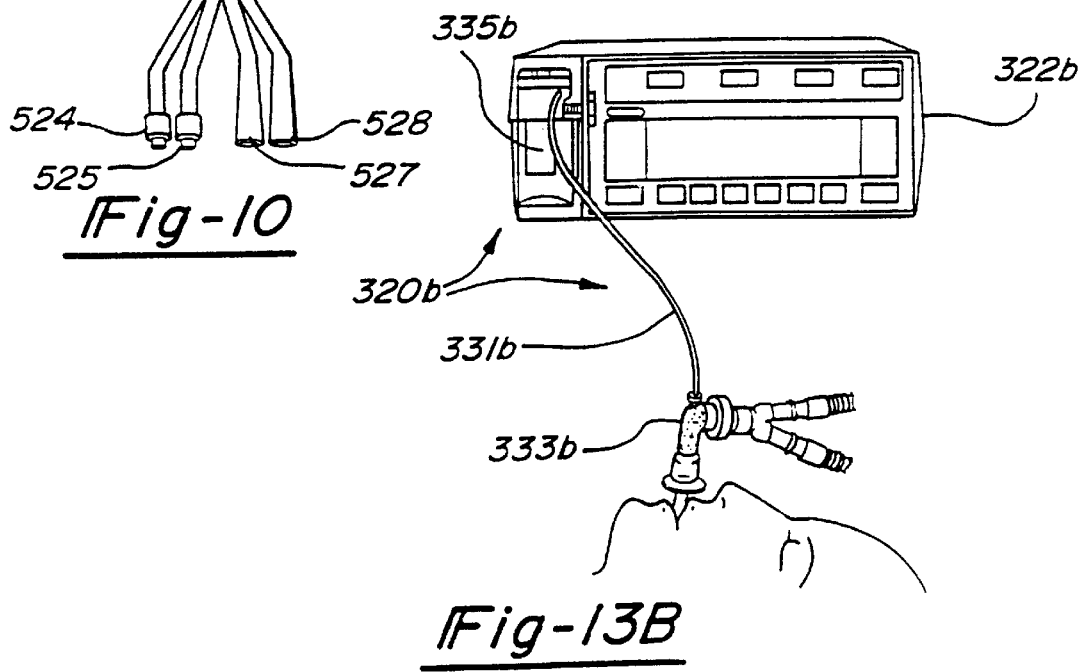

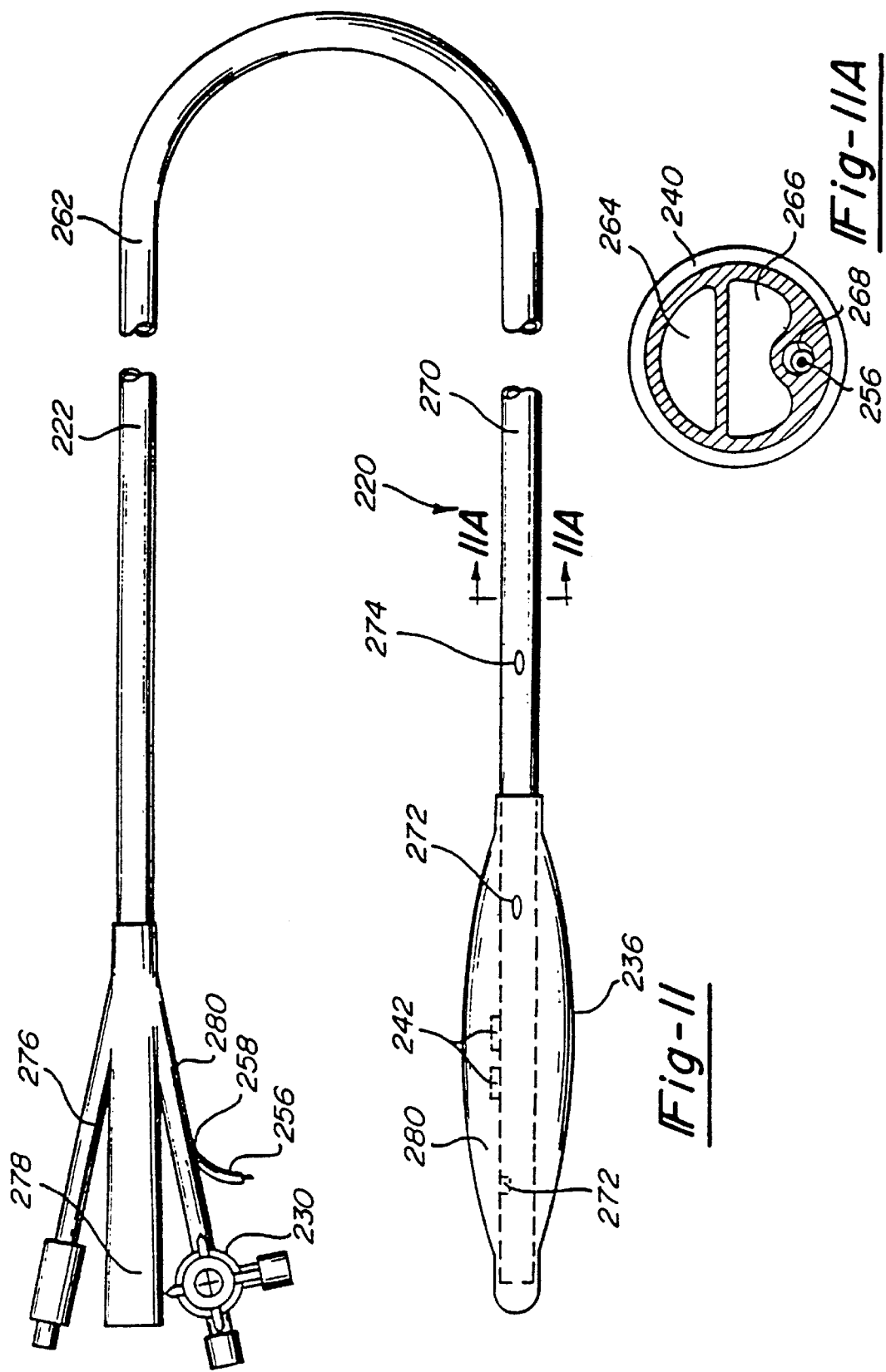

REMOTE SENSING TONOMETRIC CATHETER APPARATUS AND METHOD

This application is a continuation-in-part of U.S. patent application Ser. No. 035,020, filed Mar. 22, 1993, which was a continuation-in-part of U.S. patent application, Ser. No. 014,624, filed Feb. 8, 1993, which was a continuation-in-part of copending U.S. patent application, Ser. No. 719,097, filed Jun. 20, 1991, which was a continuation-in-part of copending U.S. patent application, Ser. No. 994,721, filed Dec. 22, 1992.

This application hereby expressly incorporates by reference, the disclosures and drawings of the following issued U.S. patents: U.S. Pat. Nos. 4,221,567; 4,233,513; 4,273,636; 4,423,739; 4,576,590; 4,480,190; 4,596,931; 4,643,192; 4,671,287 4,859,858; 4,859,859; 4,907,166; 4,914,720; 5,042,522; 5,067,492; 5,095,913; 5,158,083; 5,174,290; and 5,186,172.

BACKGROUND AND SUMMARY OF THE INVENTION

This invention relates to medical diagnostic equipment and methods and is particularly concerned with hollow viscus tonometry and remote electronic and optical sensing.

Until the advent of the tonometric method (see U.S. Pat. No. 4,643,192, issued Feb. 17, 1987) few considered any aspect of acid-base balance when attempting to monitor or maintain the adequacy of tissue oxygenation. Yet acid-base balance is primarily determined by the balance between the protons released during the release of energy by ATP hydrolysis and the resynthesis of ATP by oxidative phosphorylation. The hydrolysis of ATP generates 150,000 mmols of H+ each day in a resting 70 Kg man. All, but the 1% of this fixed acid load excreted by the kidneys each day, is presumed to be consumed in the resynthesis of ATP by oxidative phosphorylation. When the delivery of oxygen fails to satisfy the energy needs of the tissue the rate of ATP hydrolysis exceeds the rate of synthesis and the pH falls as the degree of unreversed ATP hydrolysis increases.

Information for determining global tissue oxygenation has been collected for many years. Eoda, D., "'Gastrotonometry' an Aid to the Control of Ventilation During Artificial Respiration," *The Lancet* (1959). However, it is now widely accepted that global measurements of oxygen delivery, consumption and extraction do not provide reliable information about the adequacy of local or even "global" tissue oxygenation in patients. The indirect measurement of gastric intramucosal pH (pHi) as described in U.S. Pat. Nos. 4,643,192; 5,158,083; 5,186,172 provides clinicians with a minimally invasive yet sensitive means of detecting the development of a tissue acidosis, and hence inadequacy of tissue oxygenation, in a region of the body that is one of the first to exhibit an inadequacy of tissue oxygenation in shock. Use of the measurement has revealed that some 50% to 60% of patients having major surgery and 80% of ICU patients develop an intramucosal acidosis during their illness despite the conventional appearance of being adequately resuscitated.

The degree and duration oL the presence of a gastric intramucosal acidosis are highly sensitive measures of the risk of developing ischemic gut mucosal injury and its putative consequences, namely the translocation of bacteria and their toxins, cytokine release, organ dysfunctions and failures, and death from the organ failures. By providing an index of the adequacy of tissue oxygenation in one of the first parts of the body to exhibit dysoxia in shock the measurement of gastric intramucosal pH improves the opportunity to obtain advanced and accurate warning of impending complications and to intervene in time to prevent them. More importantly timely therapeutic measures that restore the intramucosal pH to normality and "gut-directed" therapies incorporating measures that reverse an intramucosal acidosis are associated with an improved outcome. "pH-directed" therapy has in addition been shown to improve outcome in a prospective randomized multicenter study of medical and surgical ICU patients.

The measurements of gastric intramucosal pH have revealed deficiencies in currently accepted practices. It has, for example, become apparent that empirical increases in global oxygen delivery may be redundant in some 40% to 50% of patients having major cardiovascular surgery who do not develop a gastric intramucosal acidosis and whose prognosis is excellent. It is further apparent that the vogue of increasing global oxygen delivery to supranormal levels cannot be relied upon to prevent or to reverse the presence of an intramucosal acidosis. Of particular concern is the intramucosal acidosis that may be induced by measures, notably the transfusion of red blood cells and dobutamine, that increase global oxygen delivery in patients who do not have an intramucosal acidosis but whose global oxygen delivery is considered too low.

THE TONOMETRIC METHOD

The measurement of pH in the most superficial layer of the mucosa is obtained indirectly by measuring the partial pressure of carbon dioxide ($pCO_2$; $pCO_2$) in the lumen of the gut and the bicarbonate concentration in arterial blood and substituting these two values in the Henderson-Hasselbalch equation or some modification thereof. See "Gastric Intramucosal pH as a Therapeutic Index of Tissue Oxygenation in Critically Ill Patients," *Lancet* 1992; 339; 195–99, incorporated herein by reference. The indirect measurement of the pH of the wall of the organ (pH indirect or intramucosal pH) may be employed because it is believed or assumed that the $pCO_2$ in the most superficial layers of the mucosa is in equilibrium with that in the lumenal contents with which it is in contact. It is further based upon the assumption that the bicarbonate concentration in the tissue is the same as that being delivered to it in arterial blood and that the pKa, 6.1, is the same as that in plasma.

At present, measurements of pCO2 in the lumen of the stomach are obtained by infusing saline into the silicone balloon of a gastrointestinal tonometer, allowing the $pCO_2$ in the saline to equilibrate with that in the lumen of the gut; recording the equilibration time; aspirating the saline; measuring the $pCO_2$ in the saline with a blood gas analyzer; using a nomogram to derive the steady-state adjusted pCO2 from the equilibration time and the measured $pCO_2$; and then derive the intramucosal pH from the steady-state adjusted $pCO_2$ obtained and the bicarbonate concentration in a substantially contemporaneous sample of arterial blood. Again, see U.S. Pat. Nos. 4,643,192, issued Feb. 17, 1987; U.S. Pat. No. 5,174,290, issued Dec. 29, 1992; and U.S. Pat. No. 5,186,172, issued Feb. 16, 1993; as well as copending U.S. applications, Ser. No. 719,097, filed Jun. 20, 1991; Ser. No. 994,721, filed Dec. 22, 1992 and Ser. No. 014,624, filed Feb. 8, 1993; all three issued patents being completely and expressly incorporated herein by reference. The precision of the measurement of gastric intramucosal pH between healthy subjects is excellent, the gastric intramucosal pH in a healthy subject being the same as the pH in his arterial blood.

The prior art (see U.S. Pat. No. 4,643,192) has recognized that intestinal ischemia, and to a lesser degree, stress ulceration, are two problems that plague physicians involved in the management of patients in intensive care units. Intestinal ischemia, in particular, has an insidious onset and may not be detected until days after the intestine has become completely and irreversibly compromised. A delay in the diagnosis of intestinal ischemia may have devastating consequences for a patient. The availability of means for early diagnosis and management of patients with these problems would have immediate applicability in all intensive care units, especially where the procedure can be conveniently conducted with reasonable safety and reliability.

It has been established that a fall in the intramucosal pH may precede the development of intestinal ischemia and stress ulceration. As discussed in U.S. Pat. No. 4,643,192, which is expressly incorporated herein by reference, entitled "Hollow Viscus Tonometry" a fall in intramucosal pH also occurs within minutes of inducing intestinal ischemia in dogs. The fall in pH in intestinal mucosa, and hence the likelihood of Ischemia or stress ulceration, can be reliably calculated from a $pCO_2$ (partial pressure of $CO_2$) I or other indicia of pH, in lumenal fluid and the bicarbonate concentration in arterial blood. The method of calculating the pH in intestinal mucosal tissue, pursuant to principles set forth in prior related patents discussed herein, has been validated by directed measurements under a variety of conditions simulating clinical problems. A correlation coefficient on the order of 0.92 to 0.95 has been obtained in each of 16 dogs. The validity of the procedure is inherently extensible to humans, and indeed may also be useful in assessing the vitality of other hollow organs and tissue. See R. G. Fiddian-Green et al. "Splanchnic Ischemia and Multiple Organ Failure".

To measure the $pCO_2$ in the lumen of the gut it has heretofore been necessary to obtain and remove a sample of fluid that has been in contact with the wall of the gut for a certain time period, usually at least half an hour. It has now been observed that it is somewhat difficult to manually aspirate the sampling fluid or medium from a tonometric catheter located in the gut or other internal focus with any consistency. It is much easier to obtain such samples from the stomach, but samples obtained from the stomach frequently contain foreign material that can damage a gas analyzer.

As taught in prier related patents discussed herein, the desired sample or samples can be obtained from the gut using a catheter tube (called a tonometric catheter) having a walled sampling chamber on the tube with the sampling chamber being in sample-specific communication with the hollow interior of the tube. The wall of the sampling chamber comprises a material which is substantially impermeable to liquid yet is highly permeable to gas. One suitable material is polydimethylsiloxane elastomer.

In use the catheter is introduced into a patient to place the sampling chamber at a desired site within the gut (or other hollow organ) An aspirating liquid or medium is employed to fill the interior of the sampling chamber. The sampling chamber is left in place at the desired sampling site long enough to allow the gases present to diffuse through the wall of the sampling chamber into the aspirating liquid. The time should be long enough for the gases to equilibrate. The liquid impermeable nature of the sample chamber wall material prevents both the aspirating liquid from leaking out of the chamber and also the intrusion of any liquids into the aspirating liquid. After the appropriate or desired amount of placement time has elapsed the aspirating liquid is aspirated along with the gases which have diffused into it. The sample thus obtained is analyzed for gas content, in particular for $pCO_2$. In this way the $pCO_2$ within the lumen of the gut can be reliably measured with the fluid being free from lumenal debris.

In carrying out the diagnostic method taught in prior related patents, the $pCO_2$ measurement is utilized in. conjunction with a measurement of the bicarbonate ion concentration ($HCO_3^-$) in an arterial blood sample of the patient for determining the pH of the tract wall.

Depending upon the particular condition of a given patient, the catheter may be left in place and samples may be taken at periodic intervals so that pH values may be periodically calculated. The procedure has a high reliability in accurately determining the adequacy of organ tissue oxygenation, and diagnosing intestinal ischemia in its incipient stages. Such determination or detection can be useful in treating the patient so that the potentially devastating consequences resulting from less timely detection may often be avoided.

While the sampling techniques taught in the prior related patents discussed herein have provided highly accurate and reliable results, it has now been observed that there are instances (in the care of the critically ill in intensive care units, for example) in which remote sensing of the organ or organ-wall condition and automatic determination or calculation of the organ or organ-wall pH would be advantageous and easier to effectuate. This method would thus partially or totally eliminate the need for the somewhat cumbersome manual aspiration of the sampling fluid or medium which fills the sampling chamber. There is also a need to extend the benefits of tonometric sampling and sensing to other internal hollow viscus organs. To this end, there is a need for new and different tonometric devices specifically adapted to allow sensing and sampling techniques to be performed with ease in a clinical environment, and in combination with other procedures.

The importance and significance of determining the pH of the wall of a given hollow viscus organ has been recently dramatically magnified as a result of the recent recognition that the oH of the wall of a given organ can be employed to accurately evaluate the vitality and/or stability of that organ as well as others; this is in contrast to merely determining whether such an organ is experiencing an ischemic event. Further, certain organs can be selected for monitoring, either alone or in combination, and evaluation of this organ or these organs can aid in predicting the overall condition of the patient, or the onset of a multitude of pathologies, including predicting or identifying such events as multiple organ failure. Such a methodology can be employed to greatly enhance and supplement the monitoring of the critically ill, for example.

It has also been observed that an unusually large negative bias is encountered when measuring the $pCO_2$ in saline with certain blood gas analyzers (including those manufactured by Nova Biomedical, L. Eschweiler and Mallinckrodt) that have been standardized for blood but not for saline. The presence or absence of unacceptable bias may be determined by the use of reference samples of tonometered saline. The inter-instrumental bias encountered when measuring arterial blood gases and especially $pCO_2$ in saline with different blood gas analyzers requires that each institution derive its own normal values for meaningful use in clinical practice. It is reported that the precision of the measurements made within a static environment may be improved and unacceptable interinstrumental bias eliminated, in whole or in part, by using Gelofusine® (sterile 4% w/v succinylated gelatine in saline), a phosphate buffer, bicarbonate-buffered saline, or mixtures thereof. Unfortunately the diffusional characteristics may be altered, in which case the nomograms provided for the determination of steady-state adjusted $pCO_2$ in saline cannot be used for the determination of intramucosal pH with these fluids.

The time constant may be reduced to seconds by using an electrochemical $pCO_2$ sensor directly in the lumen of the gut and measuring the $pCO_2$ in either liquid or gaseous luminal contents, as described herein. Unfortunately, $pCO_2$ sensors are known for their tendency to drift and cannot be easily recalibrated in vivo.

In one aspect, the present invention provides a new apparatus and method for remotely sensing organ condition and conveying a signal, e.g. an electrical current or optical signal, to an electronic or optical apparatus located outside the organ under investigation. In one embodiment, a transducer (or plurality of transducers) is attached to a tonometric catheter for introduction into the organ along with the tonometric catheter. This first sensor generates and conveys a signal indicative of some desired aspect of organ condition, e.g., indicative of the $pCO_2$, pH and/or $pO_2$ level of the organ or organ-wall. For example, in one preferred embodiment, mean ambient $pCO_2$, pH and/or $pO_2$ of lumenal fluid or the like is measured or monitored via wire or other suitable electromagnetic energy conveying means to an electronic circuit which interprets the electromagnetic signal and produces a report of the organ condition. The electronic circuit may include an input for receiving a separately determined signal indicative of the blood pH of the patient. Using this $pCO_2$, pH and/or $pO_2$ measurement alone with blood (preferably arterial) pH data, the electronic circuit determines the pH of the organ under test and thereby provides information for determining the organ's current condition or perhaps predicting the organ's future condition. The electronic circuit may be suitably constructed from analog components, digital components or both.

In another embodiment, a pH, $pCO_2$ or $pO_2$ sensitive calorimetric substance is injected into an area adjacent to the organ, e.g., into the sampling chamber of the tonometric catheter, and an optical sensor is employed to detect color change in order to determine the pH of the wall of that organ. The optical sensor can either be disposed in or on the tonometric catheter for introduction into the area adjacent the organ or it may be disposed outside the organ with fiber optic cable optically coupling the sensor to the tonometric catheter site at which the pH sensitive substance has been injected.

In another aspect the present invention provides a variety of new and different tonometric catheter devices for sensing and/or sampling a fluid or gas property (such as pH, $pO_2$, $pCO_2$, and the like) which is indicative of the condition o an internal organ, in conjunction or combination with a walled catheter tube adapted for delivery or draining fluids, such as nasogastric tubes, urinary catheters, ureteric catheters, intestinal feeding tubes, wound or abdominal drains (suction or regular) and biliary tubes, or other catheters and stents, with or without remote sensing means for pH, $pCO_2$ and/or $pO_2$.

In still another aspect or embodiment, the device employs two separate walled catheter tubes, one tonometric catheter tube for the measurement of a fluid or gas property, that is in communication with the sampling chamber; and a second walled catheter tube adapted for delivering or draining fluids.

In yet another aspect or embodiment, the device employs a walled sampling chamber in communication with a sensing means, and a second walled catheter tube adapted for delivering or draining fluids.

Although not originally thought to be feasible or efficacious, the present invention in yet another embodiment has also accomplished improved accuracy and speed by the effective infrared sensor measurement of liquid or gaseous fluid parameters or compounds of interest, such as $pCO_2$, anesthetic gases, etc., admixed in a gaseous sampling medium, preferably air. This was previously not believed to be possible due to the high gas volumes typically required for accurate infrared measurements, and because of erroneous measurements resulting from increased gas densities caused by higher tonometric sampling medium pressures.

In view of all of the above, it will be appreciated that tonometric method can now be modified in a fashion that provides the advantages of reduced equilibration time (with respect to saline) and without the need to recalibrate the sensor in vivo, or remove it for recalibration. In the improved method, and very generally, air is employed as the medium, and measurements can be taken either in discreet samples or continuously. The sampling medium air is aspirated from the walled sampling chamber of a tonometric catheter which has been inserted into the organ of interest (e.g., the gut). The $pCO_2$ of the aspirated sample is measured by employing a side-stream or main-stream, drift-free, non-dispersive infrared gas analyzer. The $pCO_2$ value obtained is then compared with either (1) the arterial bicarbonate value and/or (2) another direct or indirect measurement of a "global" or "systemic" physiologic value (e.g., pH, $pCO_2$ or $pO_2$ of arterial, venous, umbilical or capillary blood; mixed venous bicarbonate; arterial oxygen saturation (e.g., as measured by pulse oximetry); end-tidal $pCO_2$; transcutaneous ($TCpCO_2$) $pCO_2$) in order to make a determination of the condition of the organ or if (A) a bicarbonate value must be obtained and/or (B) what, if any, clinical therapy or intervention may be necessary or appropriate with respect to oxygenation of the organ of interest.

In some embodiments, a Raman spectrometer may be employed, either in line or side stream, in place of the IR gas analyzer, as it will be appreciated by those skilled in the art that Raman spectroscopy offers distinct advantages over the more direct infrared-type measurements in certain applications.

A preferred indirect measurement of a "global" or "systemic" $pCO_2$ value is an end-tidal $CO_2$ value, or a transcutaneous $CO_2$ value.

The present invention can successfully use a gaseous sampling medium, such as air, along with known commercially available non-dispersive infrared spectrophotometry devices, resulting in high sample and measurement reliability, faster equilibration, thus allowing for faster and more frequent intermittent sampling or even continuous sampling, increased ease of use, and decreased sources of error, when compared to the prior use of a liquid sampling medium (such as saline), and a blood gas analyzer, for example.

Those skilled in the art will readily recognize the kind of non-dispersive, infrared gas analyzing devices contemplated by the present invention. Examples of these devices are those commercially available and marketed by such companies as Datex, Division of Instrumentarium Corporation or Novametrix Medical Systems, Inc., for example. Other examples of such devices and related equipment are discussed and disclosed in U.S. Pat. Nos. 4,233,513; 4,423,739; 4,480,190; 4,596,931; 4,859,858; 4,859,859; 4,907,166; 4,914,720; 5,042,522; 5,067,492; 5,095,913, the disclosures and drawings of all of which are hereby incorporated by reference herein.

Non-dispersive infrared gas analyzers in general are typically manufactured in either "side-stream" or "main-stream" configurations. In one, a sample of a volume of gas is taken from a patient's gas flow (such as respiratory gas flow, a tonometric sampling chamber gas flow, or both) and conveyed through a sample tube to the infrared sensor and analyzer; in such a device, the sample is not typically returned to the patient's gas flow. The other common type is the so-called in-stream or main-stream type, which has a sensor apparatus that mounts directly within the patient's gas flow conduit and senses and takes measurements as the gas flows past the sensor.

In this regard, a tonometric apparatus according to the invention can include a temperature measurement feature, with a built-in thermistor, either in the catheter device or the sampling chamber itself, or in the system's processing instrumentation, to measure the sample temperature as an indication of body core temperature and for purposes of calibrating or correcting $pCO_2$ (or other parameters) calculations. Such a feature is especially desirable in systems using gas samples, due to the volumetric responses of the gas to changes in temperature.

For further understanding of the invention, its objects and advantages, reference may be had to the following specification, the accompanying drawings, and the information incorporated herein by reference. Also, see our co-pending and commonly assigned applications Ser. No. 719,097, filed Jun. 20, 1991; Ser. No. 994,721, filed Dec. 22, 1992; and Ser. No. 014,624, filed Feb. 8, 1993, all of which are completely and expressly incorporated herein by reference.

BRIEF DESCRIPTION OF THE DRAWINGS

FIG. 1 is a view of a first embodiment of the tonometric catheter;

FIG. 2 is a partial view of a tonometric catheter similar to that of FIG. 1, but having optional sensors mounted on the inside of the catheter tube;

FIG. 4A is a cross-sectional view of the tonometric catheter of FIG. 4 taken substantially along the line 4A—4A of FIG. 4;

FIG. 4B is a cross-sectional view of the tonometric catheter of FIG. 4 taken substantially along the line 4B—4B of FIG. 4;

FIG. 5A is a cross-sectional view of the tonometric catheter of FIG. 5, taken substantially along the line 5A—5A of FIG. 5;

FIG. 10 is a view of one example of a tonometric catheter in combination with a urinary catheter;

FIG. 11 is a view of another embodiment of a tonometric catheter in combination with a urinary catheter;

FIG. 11A is a cross-sectional view of the tonometric catheter/urinary catheter of FIG. 11, taken substantially along the line 11A—11A of FIG. 11;

FIG. 13A is diagrammatic representation of an exemplary in-stream, non-dispersive infrared gas analyzer system usable in the present invention;

FIG. 13B is a diagrammatic representation of an exemplary side-stream, non-dispersive infrared gas analyzer system in the present invention;

DETAILED DESCRIPTION OF THE PREFERRED EMBODIMENTS

Figure 3:
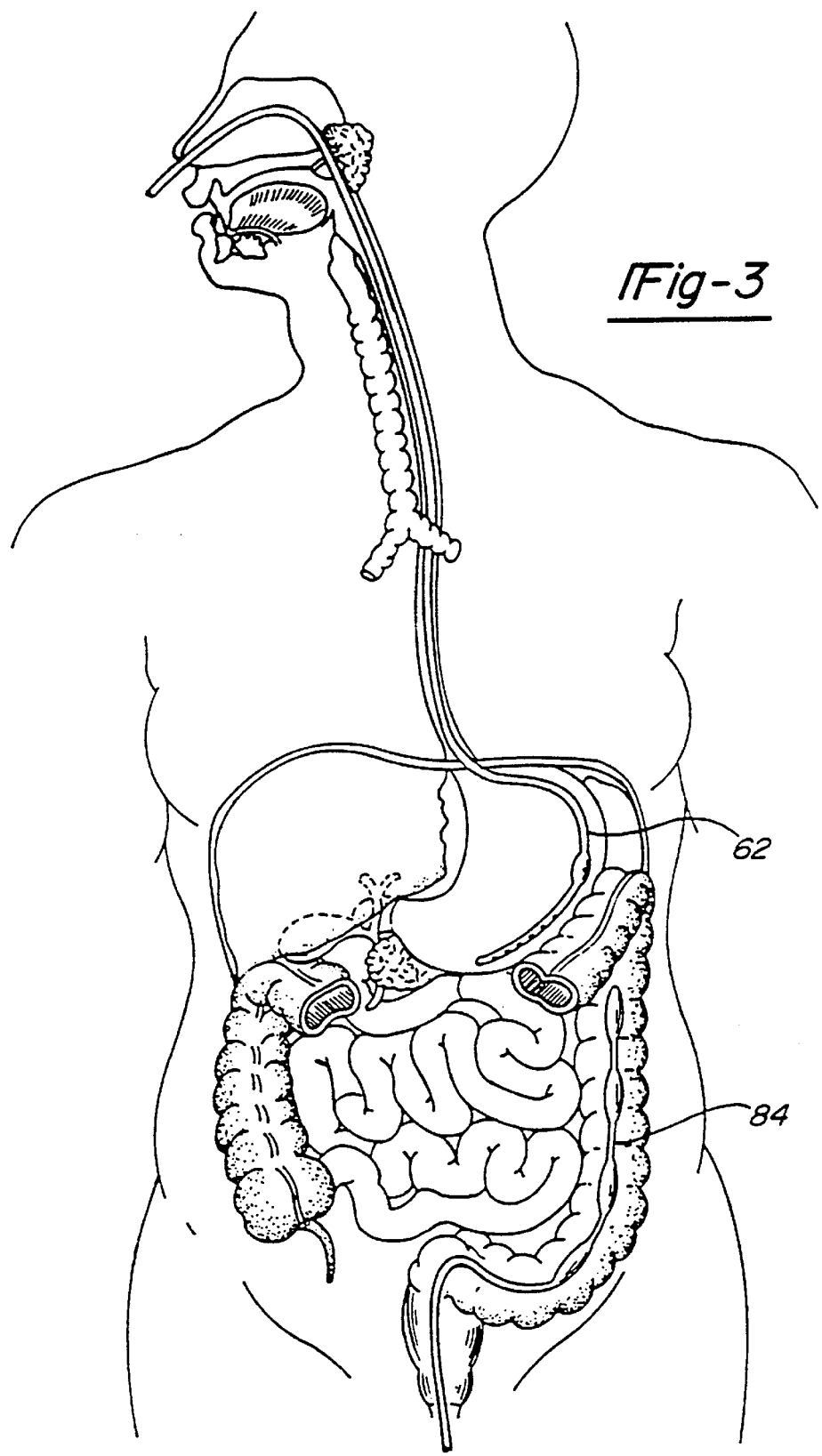
FIG. 3 illustrates the method of use of an exemplary tonometric catheter in measurement of the $pCO_2$ of the colon and also of the stomach, the specific embodiment illustrated for colonic measurement being that of FIG. 5 and the specific tonometric catheter for gastric measurement being that of FIG. 4.

FIG. 1 illustrates a first embodiment of tonometric catheter 20. The tonometric catheter comprises a length of suitable tubing 22, one end 32 of which is closed, and the opposite end of which has a connector such as a luer-lock 24. Luer-lock 24 is adapted to receive a complementary fitting 26, which in turn couples through a second length of tubing 28 to a three-way stopcock 30. Three-way stopcock 30 may be used to selectively connect tubing 28 to various sources of irrigation or aspiration. Other fittings can be used, depending on the particular application, including those wherein a tonometric catheter is used in conjunction with an infrared sensing device, a Raman spectroscopy device, or the like.

Adjacent the closed end 32, tubing 22 is perforated as at 34. A balloon-like tonometric catheter membrane 36 is fitted over the closed end so that the perforations 34 are enclosed, as illustrated. The tonometric catheter membrane 36 has an internal sleeve diameter at 38 which forms a tight fit with tubing 22. The preferred form of tonometric catheter membrane is polydimethylsiloxane elastomer. The membrane may be sealed to the tubing 22 with appropriate adhesive so that the tonometric catheter membrane is sealed in a closed relationship to the outer wall of tubing 22, thereby forming a sampling chamber 40 adjacent closed end 32. The tonometric catheter membrane has a certain elasticity to allow the membrane to expand when filled with an aspirating fluid (liquid or gas).

The membrane 36 is preferably constructed such that at least a portion of it is selectively permeable to the liquid or gas fluid property of interest. In a preferred embodiment, it is selectively permeable to carbon dioxide, and oxygen, so that $pCO_2$ and/or $pO_2$ can be measured. It is also preferably impermeable to other materials that would interfere with the desired measurements, such as proteins and the like. In a highly preferred embodiment, a gas permeable membrane is employed.

Bonded to either the inner wall (see FIG. 2) or the outer wall of tubing 22 are one or more sensors 42 for detecting a property indicative of $pCO_2$, $pO_2$, and/or temperature. Two such sensors are illustrated in FIG. 1, bonded to the outside wall of tubing 22 with suitable adhesive. FIG. 2 illustrates the sensor attached to the inner wall of tubing 22.

In a preferred embodiment, at least a portion of the tubing, but not necessarily all of it, is made of a $CO_2$ impermeable material, such as those based on polyurethanes, PVC's, or polyester elastomers derived from the reaction of dimethylterephtalate 1,4-butanediol and $\alpha$-hydro-$\Omega$-hydroxypoly (oxytetramethylene). In preferred embodiments, this material can be PVC or polyurethane.

For purposes of sensing temperature, thermistor devices are presently preferred.

The sampling chamber 40 can be filled with an aspiration or sampling medium (gaseous or liquid) that is used to absorb or otherwise provide a means for incorporating and delivering or measuring the liquid or gaseous fluids of interest. Such a medium is selected depending upon many factors, including the properties of the liquid or gaseous fluids of interest, the type of sensor 42 employed, and the type of calibration that is necessary. Such mediums include air, bicarbonate solutions, bicarbonate-buffered solutions, phosphate-buffered solutions and saline solution. It might be noted that gases often behave as fluids and are therefore frequently considered to be fluids.

As noted above, when the sensor employed does not require frequent recalibration, the need for the sampling chamber 40 to be in communication with the proximate end of the tonometric catheter (that remains outside the patient) may be eliminated since no aspiration is needed. However, in many instances such communication may still be desirable as aspiration may be required to calibrate the sensor or sensors, to replace the aspirating or sampling medium with a fresh medium, and to incorporate the gas or gases of interest.

Figure 4:
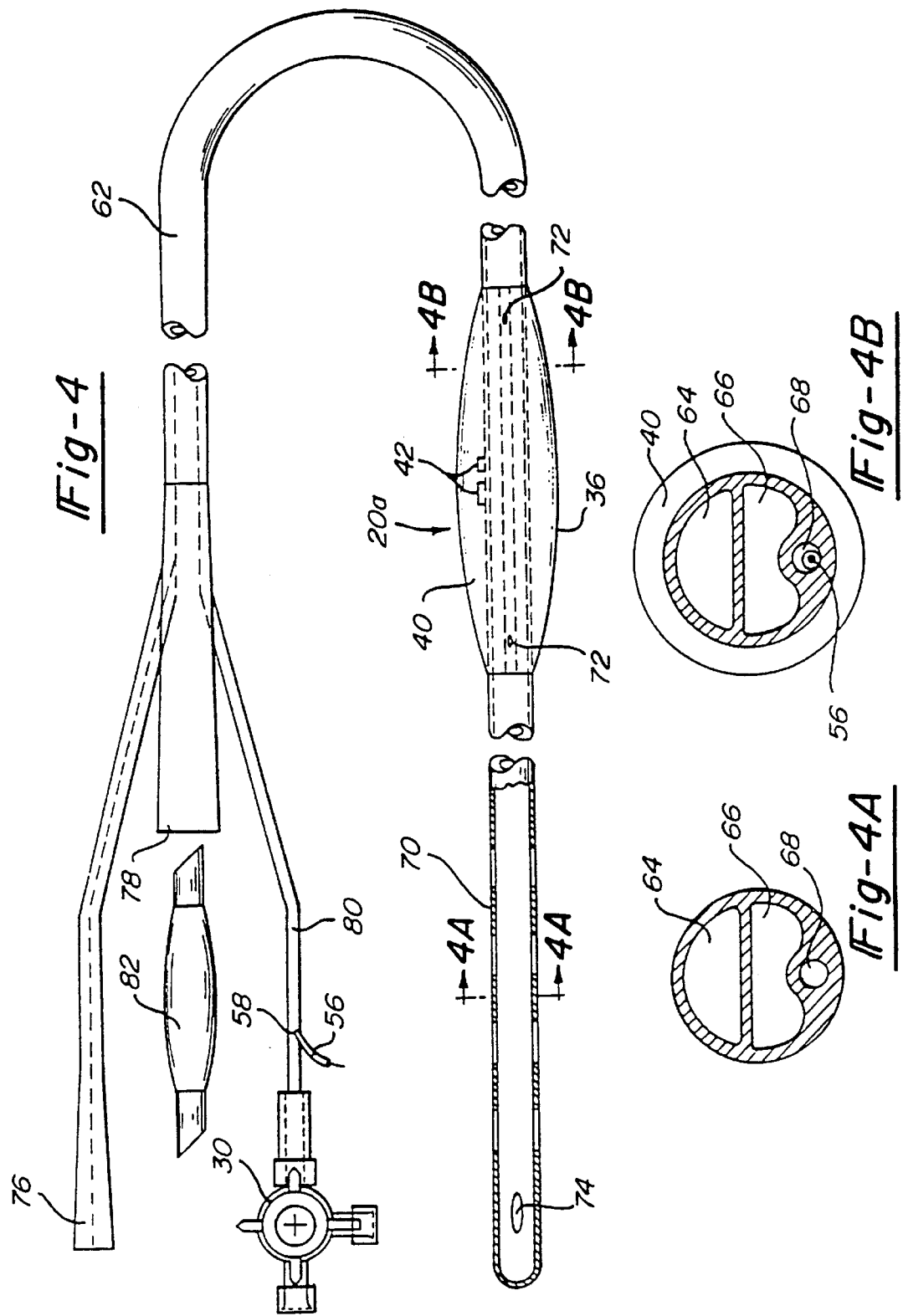
FIG. 4 is another embodiment of the tonometric catheter with nasogastric tube.

Another embodiment of the tonometric catheter is illustrated in FIGS. 4, 4A and 4B. As illustrated, the tonometric catheter can be appropriately configured to also serve as a nasogastric tube, either with or without an air lumen. With reference to FIG. 4, the tonometric catheter 20a comprises a multipassage tubing 62 which defines three individual passageways or lumens, an optional air lumen 64, a suction lumen 66 and a tonometric catheter lumen 68. A tonometric catheter membrane, similar to that previously described, is attached at an intermediate location on tubing 62, allowing a portion of the tubing to extend beyond the end of membrane 36 to define the nasogastric tube 70, or a portion thereof. Tubing 62 is provided with a plurality of perforations 72 which communicate between tonometric catheter lumen 68 and the sampling chamber 40 defined by membrane 36. If desired, one or more sensors 42 can be included in accordance with the above teachings, in which case a suitable conductor 56 may be routed through tonometric catheter lumen 68 to exit at sealed aperture 58.

The nasogastric tube 70 is suitably provided with a plurality of openings 74 through which the stomach may be aspirated.

At the opposite end of tubing 62 the tubing splits to form three separate connections. Optional air lumen 64 communicates with optional air lumen passageway 76, suction lumen connects with suction lumen passageway 78 and tonometric catheter lumen 68 communicates with tonometric catheter lumen passageway 80. The tonometric catheter lumen passageway is fitted with three-way stopcock 30, similar in function and purpose to the three-way stopcock 30 described in connection with FIG. 1. If desired, a quick connect fitting 82 may be used to couple the suction lumen passageway 78 with an aspiration source. As illustrated, the quick connect fitting preferably has angularly cut ends and a slightly enlarged midsection, making it easy to insert into the end of passageway 78 and also into the aspiration hose coupling (not shown). The enlarged midsection helps form a seal with the adjoining passageways. Preferably the quick connect fitting is fabricated of disposable plastic.

Figure 5:
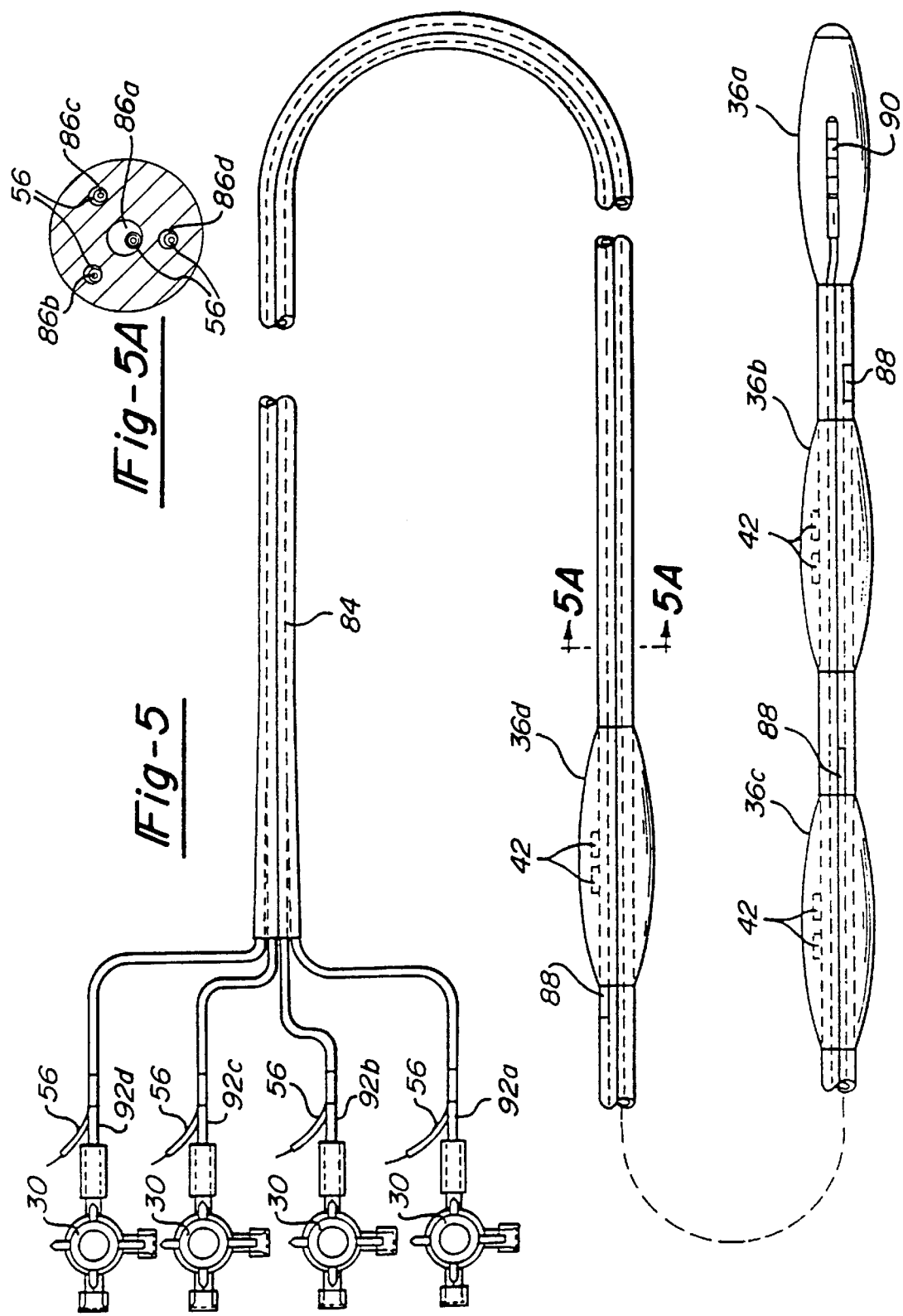
FIG. 5 is yet another embodiment of the tonometric catheter having multiple sensing/sampling portions.
Figure 6:
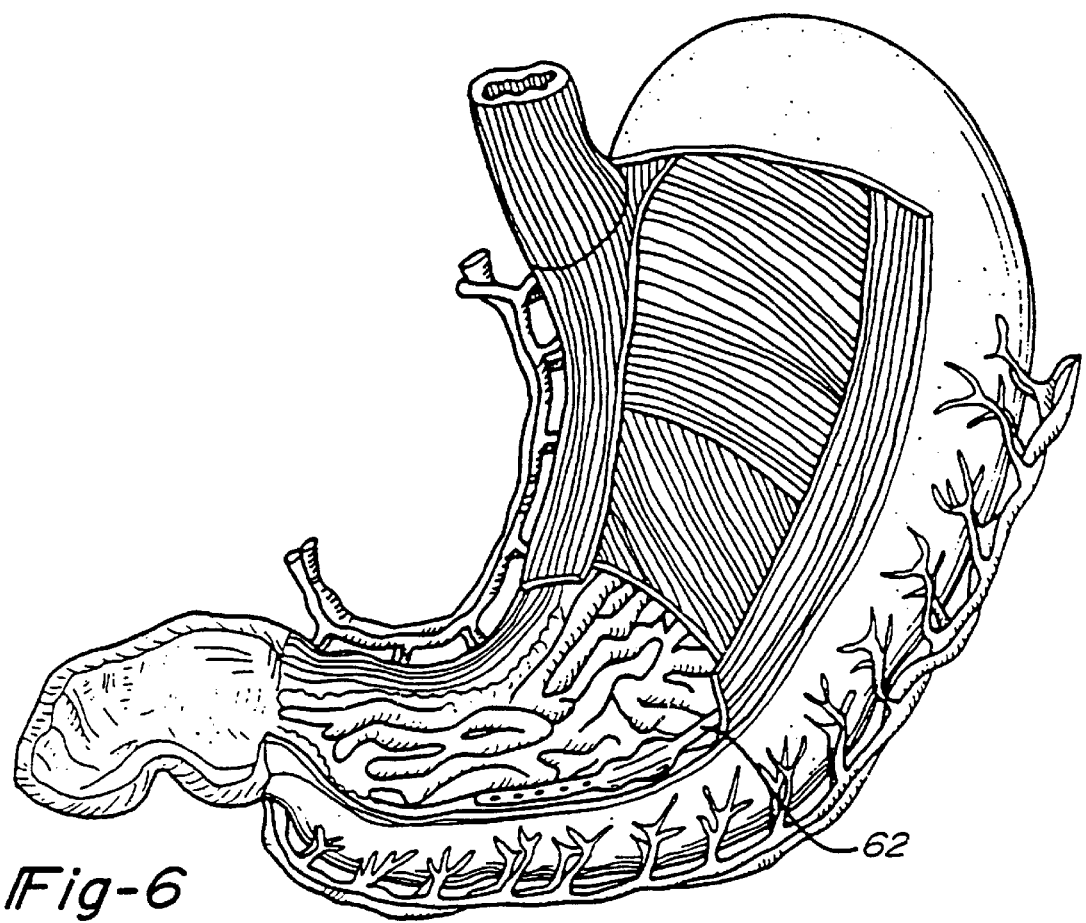
FIG. 6 is a detailed view illustrating the tonometric catheter of FIG. 4 in use within the stomach.
Figure 7:
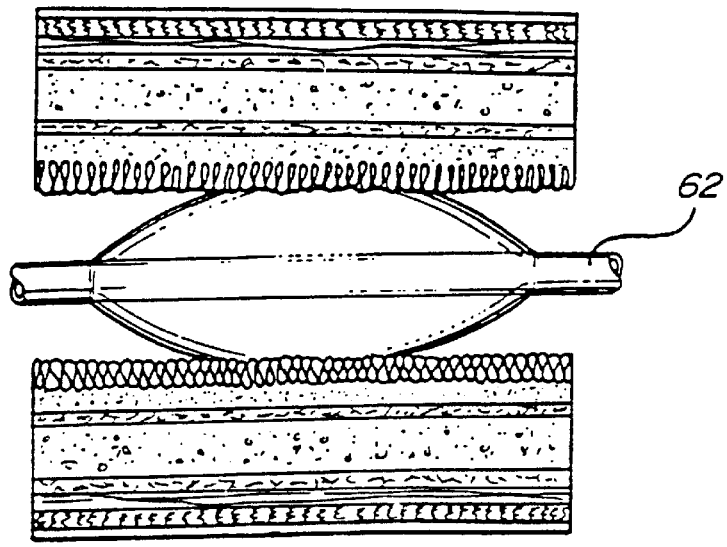
FIG. 7 is a detailed view illustrating the tonometric catheter of FIG. 5 in use within the colon.
Figure 8:
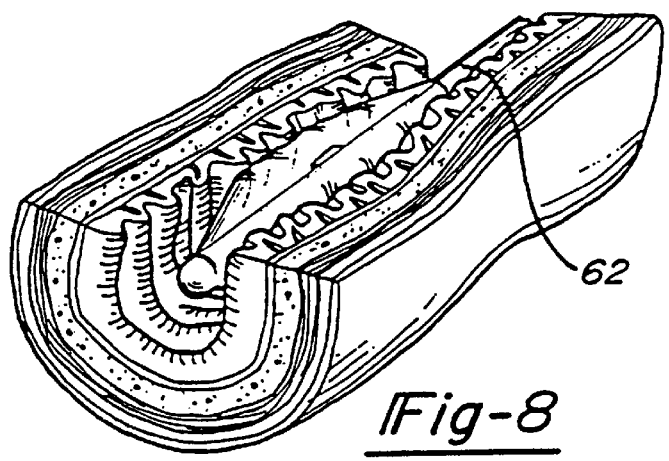
FIG. 8 is a similar view illustrating the tonometric catheter of FIG. 1 in use within the colon.

Yet another embodiment of the tonometric catheter is illustrated in FIGS. 5 and 5A. This embodiment is a multiple tonometric catheter embodiment employing a tubing 84 having a plurality of passageways or lumen as shown in the cross-sectional view of FIG. 5A. Specifically, tubing 84 includes an air lumen 86a which communicates with the endmost sampling chamber 36a and three additional tonometric catheter lumens 86b, 86c and 86d, which communicate respectively with sampling chambers 36b, 36c and 36d. As with the other embodiments, each sampling chamber may be provided with one or more sensors such as sensors 42. A radiopaque tungsten plug 88 is positioned within each of the three tonometric catheter lumen 86b, 86c and 86d adjacent the distal end of each sampling chamber, serving to block the remainder of the tonometric catheter lumen passageway and thereby ensuring that fluid pressure introduced into each tonometric catheter lumen will cause the associated sampling chamber to balloon outwardly as required during use. Similarly, a radiopaque tungsten rod 90 is fitted as a plug in the end of air lumen 86a, serving to terminate the end of the air lumen passageway. Being radiopaque, the tungsten plugs and tungsten rod aid in properly positioning the tonometric catheters by being visible under fluoroscope or x-ray. In addition, if desired, tubing 84 can be provided with a radiopaque stripe along all or part of its length.

At the proximal end of tubing 84 the lumen 86a–86d diverge to define four separate tubes 92a–92d. Each tube is fitted with a three-way stopcock similar to those described above. Each sampling connector may optionally be coded numerically by color, etc. While four approximately equally spaced sampling chambers have been illustrated in FIG. 5, it will be understood that the invention can be modified to include a greater or fewer number of sampling chambers at different spacing as required for a particular application. It will also be understood that some or all of the sampling chambers can include one or more sensors coupled to conductors 56, each preferably routed through the corresponding lumen passageway.

Figure 9:
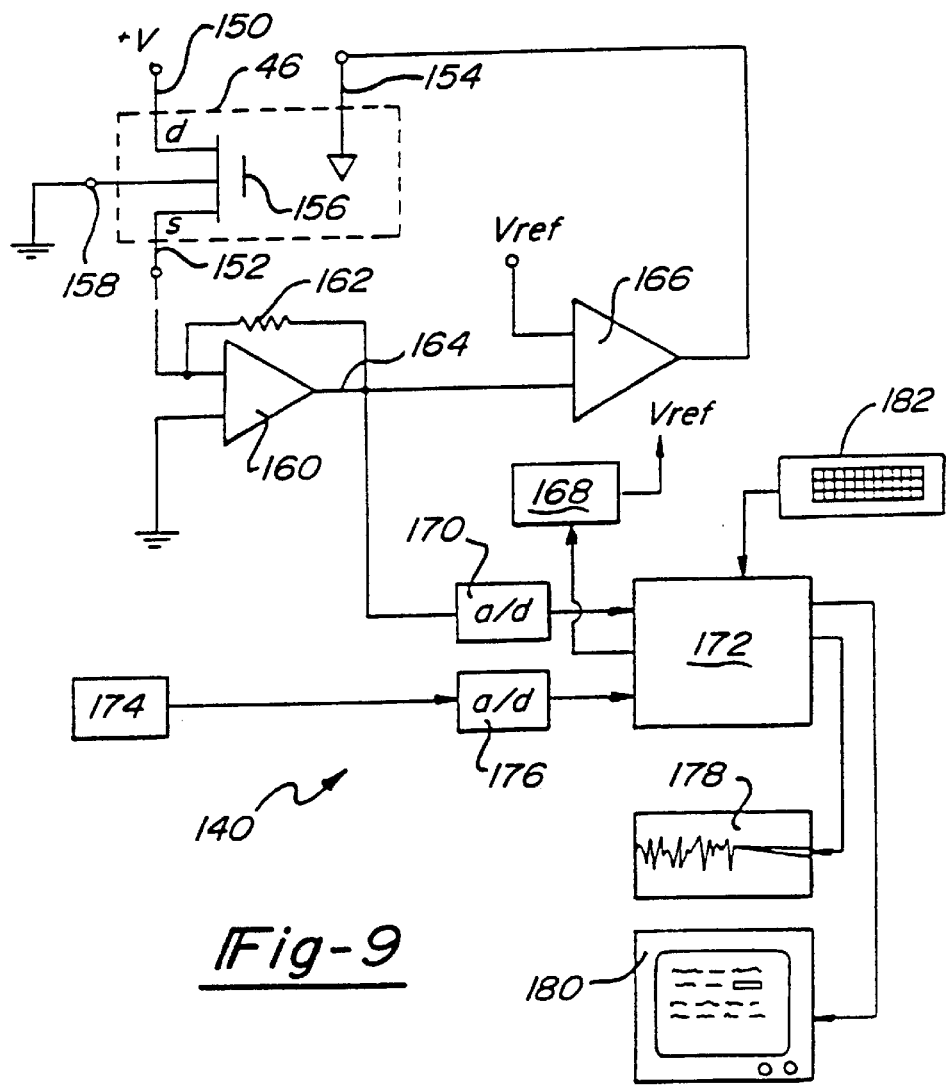
FIG. 9 is an electrical schematic diagram illustrating one embodiment of electronic circuit in accordance with the invention.

Referring now to FIG. 9, a suitable electronic monitoring circuit will now be described. In FIG. 9, a $pCO_2$-sensitive CHEMFET semiconductor device 46 has been shown schematically by the equivalent circuit model enclosed in dotted lines. The device 46 thus comprises drain electrode 150, source electrode 152 and reference electrode 154. The chemically selective system, such as a membrane system is depicted diagrammatically at 156. The substrate is grounded as at 158.

Source electrode 152 is coupled to an input lead of operational amplifier 160 which includes feedback network diagrammatically depicted at 162. Operational amplifier 160 senses the drain source current flowing through device 46 and converts this signal into a voltage signal which is output on lead 164. The drain source current changes in accordance with changes in the chemical system under test. More specifically, as the $pCO_2$ level changes in the fluid exposed to device 46, the drain source current changes accordingly. Hence the output voltage signal on lead 164 is likewise an indication of the pCO$_2$ level of the organ under test. This voltage signal on lead 164 is coupled to an input of comparator 166 which also receives a reference voltage V$_{ref}$, which may be supplied using a voltage divider network (not shown) or which may alternatively be provided by a digitally controlled voltage source 168. The output of comparator 166 is fed to reference electrode 154 to provide a stable reference bias voltage. If a digitally controlled voltage source is used, this reference voltage can be adjusted and calibrated by a computer circuit yet to be discussed. The voltage signal on lead 164 is also fed to an analog to digital convertor 170, which is in turn coupled to a microprocessor-based microcomputer 172.

In order to automatically determine the pH of the wall of the hollow viscus organ under test, a separate gas analyzer sensor 174 is used to determine the bicarbonate concentration in the arterial blood of the patient. The output of sensor 174 is coupled through analog to digital convertor 176 to microcomputer 172. Microcomputer 172 is preprogrammed to determine or calculate the pH of the organ wall using the values provided by analog to digital convertors 170 and 176. Conversion of pCO$_2$ measurements can be converted into pH measurements automatically by microcomputer 172 using various equations and references disclosed herein or others well-known in the art.

Although many different types of output devices may be employed, strip chart recorder 178 and CRT monitor 180 have been illustrated. Strip chart recorder 178 and monitor 180 are coupled as output devices to microcomputer 172. Strip chart recorder 178 offers the advantage of developing an easily readable, permanent record of the fluctuations in organ wall pH. Monitor 180 offers the advantage of providing digital readout of the pH value as well as displaying the upper and lower excursions of PH fluctuation. If desired, microcomputer 172 can be instructed and/or preprogrammed using keyboard 182 to compare the instantaneous pH value with doctor-selected upper and lower alarm limits. If the measured instantaneous pH fluctuates outside those limits, microcomputer 172 can sound an alarm to alert hospital staff.

While a single semiconductor device 46 has been illustrated in conjunction with the electronic circuit of FIG. 9, the circuit may be readily adapted for use with a plurality of semiconductor devices in order to measure the pCO$_2$ at different locations substantially simultaneously. In such an embodiment, the data coming from each sensor can be fed to a separate I/O port of microcomputer 172. In the alternative, a single I/O port can be used with the individual input signals being time multiplexed.

While some embodiments have been disclosed in connection with monitoring of the gastrointestinal tract and the urinary and ureteric tracts it will be appreciated that its principles are applicable to other hollow internal organs to monitor tissue or intramucosal pH, pCO$_2$, pO$_2$, etc., and hence perfusion of those organs. Also while several detailed constructions for tonometric catheters have been disclosed, it will be appreciated that other constructions may be developed which are equally suitable. The disclosed constructions are presently preferred for the reason that they are readily fabricated using existing available materials. Other embodiments may include other, but equivalent materials for the tonometric catheter membrane and/or connective tubing. They may also differ in the specific fabrication details. As an example, the sampling chamber may be eccentric rather than symmetric about the connective tubing.

As shown, for purposes of illustration, in FIG. 10, the tonometric catheter device according to the present invention can be employed in combination with any number of different types of urinary catheters known to those skilled in the art. By such an arrangement, the concentrations of CO$_2$ O$_2$ or other gases of interest, or other parameters, can be determined and/or monitored, and traditional urinary catheter operations can be performed, all with a single combination device.

In FIG. 10, the membrane 536 is shown incorporated into a Foley-type, three-way balloon catheter, thus making the combination Foley-type urinary and tonometric catheter a four-way catheter apparatus 520. The exemplary combination urinary-tonometric catheter includes a tonometer lumen end 524 in fluid communication with a sample chamber 540, defined by the membrane 536, in a manner essentially the same as that described above in. connection with FIG. 1 (with or without a temperature sensor). The four-way combination catheter apparatus 520 also includes the traditional three-way Foley catheter components, such as a lumen end 525 in communication with the Foley balloon 526, for purposes of balloon inflation, a lumen end 527 for drainage, and a lumen end 528 for infusing irrigation solutions in order to prevent clot retention within the bladder, the applications and functions of all are familiar to those skilled in the art.

It should be noted that although the tonometric catheter arrangement of FIG. 1 is shown in FIG. 10, merely for purposes of exemplary illustration, in conjunction with a three-way Foley-type urinary catheter, one skilled in the art will readily recognize that any of the tonometric catheter embodiments described and illustrated herein can be employed in combination with such a Foley-type urinary catheter, as well as with other familiar types of urinary catheters, such as a conical tip urethral catheter having a single eye, a Robinson urethral catheter, a whistle-lip urethral catheter, a Coude hollow olive-tip catheter, Macelot self-retaining four-wing or two-wing catheter, a Pezzer self-retaining drain, open-end head (used for cystotomy drainage), or any of a number of well-known urinary catheter types. See *Urology* 5th ed., W. E. Sanders ed. Vol. 1, p. 512 (1986).

Another embodiment of the tonometric catheter is illustrated in FIGS. 11 and 11A. As illustrated, the tonometric catheter is appropriately configured to also serve as a urinary or ureteric catheter, either with or without suction, which optionally employs sensors. With reference to FIGS. 11 and 11A, the tonometric catheter 220 comprises a multipassage tubing 262 which defines three individual noncommunicating (between each other) passageways or lumens, an optional irrigation lumen 264, a drainage or suction lumen 266 and a tonometric catheter lumen 268. A tonometric catheter membrane, similar to that previously described, is attached at a distal location on tubing 262, allowing an intermediate portion of the tubing not extending beyond the end of membrane 236 to define the uretary or ureteric catheter 270. Tubing 262 is provided with a plurality of perforations 272 which communicate between tonometric catheter lumen 268 and the sampling chamber 240 defined by membrane 236. If desired, one or more sensors 242 can be included in accordance with the above teachings, in which case a suitable conductor 256 may be routed through tonometric catheter lumen 268 to exit at sealed aperture 258.

The urinary catheter or ureteric catheter portion 270 is suitably provided with a plurality of openings 274 through which the bladder or ureters may be aspirated or irrigated.

At the opposite end of tubing 262 the tubing splits to form three separate connections. Irrigation lumen 264 optionally communicates with irrigation passageway 276, urinary lumen connects with suction or drainage lumen passageway 278 and tonometric catheter lumen 268 communicates with tonometric catheter lumen passageway 280. The tonometric catheter lumen passageway is fitted with three-way stopcock 230, similar in function and purpose to the three-way stopcock 30 described in connection with FIG. 1. If desired, a quick connect fitting 82 as seen in FIG. 4 may be used to couple the suction urinary passageway 278 with an aspiration source. As illustrated, the quick connect fitting preferably has angularly cut ends and a slightly enlarged midsection, making it easy to insert into the end of passageway 278 and also into the aspiration hose coupling (not shown). The enlarged midsection helps form a seal with the adjoining passageways. Preferably the quick connect fitting is fabricated of disposable plastic.

Yet another embodiment of the urinary catheter/tonometric catheter combination illustrated in FIGS. 11 and 11A may employ a multiple tonometric catheter embodiment employing a tubing having a plurality of passageways or lumen as shown in the cross-sectional view of FIG. 5A.

In another embodiment of the present invention, a tonometric catheter may be adopted to deliver a pharmaceutically-active agent, either for systemic, local or topical activity, or a combination thereof. For example, an additional lumen, such as the irrigation/aspiration lumen 264 shown in FIG. 11 and 11A, may be used to deliver an active agent. In another embodiment, a portion of the device may be modified so as to provide sustained release of the active agent of interest.

Thus, for example, the problems of nosocomial infection associated with catheter insertion can be overcome by incorporating an antimicrobial agent into at least a portion of the polymeric material used to manufacture the tonometric catheter, or by coating at least a portion of the device with a sustained release composition or bacteriostatic coating, or by delivering the antimicrobial via the tonometric catheter. Such modifications are well known to those skilled in the art. See U.S. Pat. No. 4,677,143, incorporated herein by reference.

Classes of useful agents include bacteriostatic coatings, antimicrobial agents, nonsteroidal anti-inflammatory agents, topical anesthetics, topical vasodilators, metabolic suppressants, and other agents that could be delivered for absorption at the sites of the tonometric catheter.

Figure 12:
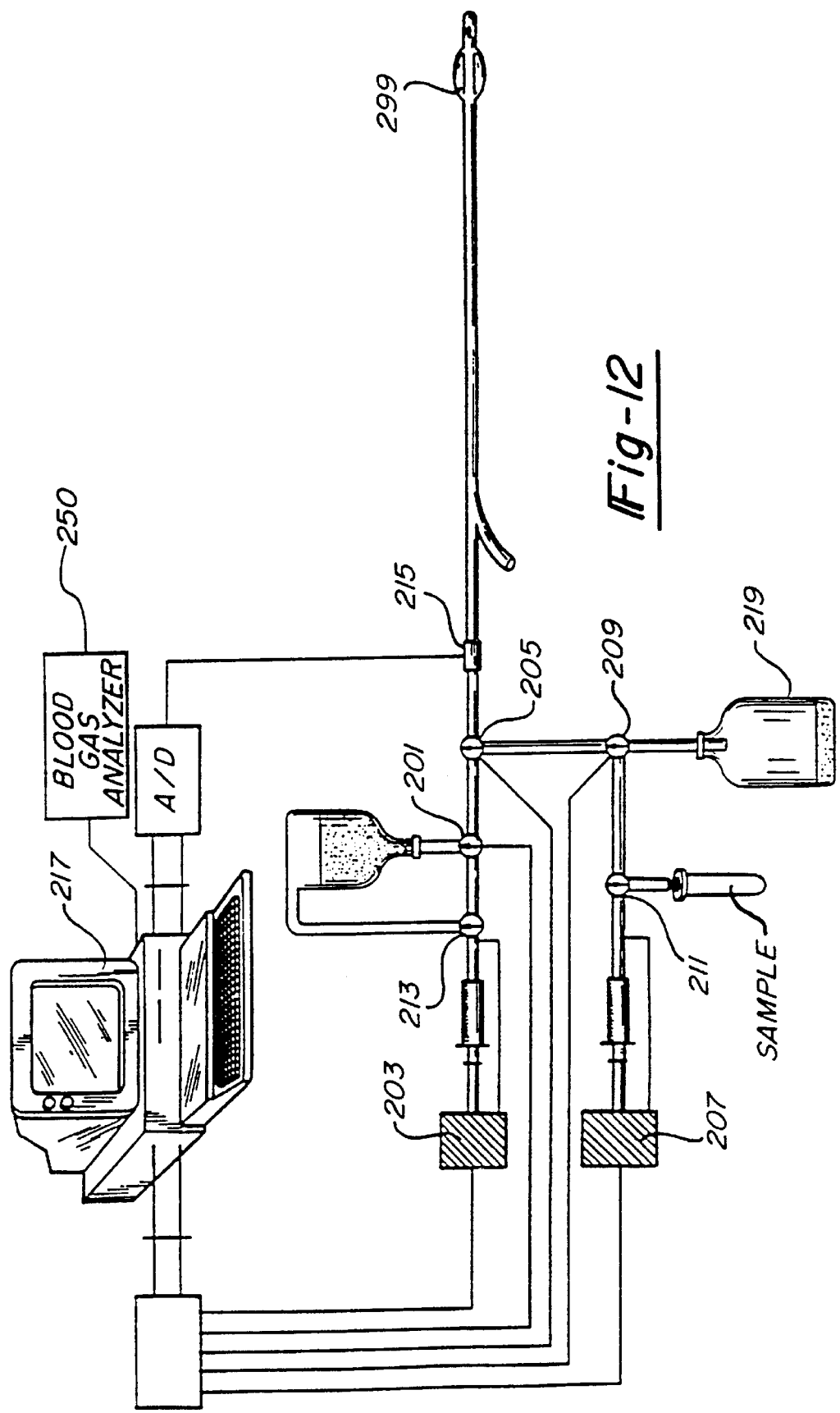
FIG. 12 illustrates one preferred example of the application of a tonometric catheter device, with remote sensing and recording apparatuses for monitoring and recording certain critical properties of interest.

In still other embodiments, conventional gas analyzers may be employed externally. A device such as that shown in FIG. 1 (or any of the exemplary catheter devices described herein) may be used in combination with a pump or aspiration means (not shown) for continuous or regular intermittent aspiration of a sample of the aspirating liquid or medium that is used to fill the sampling chamber 40. The sample removed by pump or aspiration means via attachment to the luer-lock 24 can be optionally designed so that the sample aspirated at each sampling interval can be brought in contact with an exterior, separate gas analyzing means or sensor (not shown) to determine the $pO_2$, $pCO_2$ and/or the like, of the sample. Such automatic sampling can be conducted employing a system as shown in FIG. 12. In the assembly a sampling system employs a personal computer to conduct evaluations and analysis of the samples withdrawn from the tonometric catheter 299.

Pump 203 is loaded with the sampling or aspirating medium, such as saline or air. Next, valve 201 is activated to withdraw a desired amount of the sampling fluid. The valve 201 is deactivated and pump 203 is used to infuse the sampling chamber of the tonometric catheter 299 using a calibrated amount or, optionally, until a predetermined pressure is sensed by a pressure transducer 215. The sampling fluid or medium is allowed to come to equilibrium with the wall of the organ or area of interest. Next the "dead space," i.e., the area of the lumen filled with the sampling fluid that is not in equilibrium, is removed by activating valve 205, activating pump 207, activating valve 209 and infusing pump 207; the waste 219 is discarded. A gaseous sample for analysis can then be withdrawn by deactivating valve 209, activating pump 207 to then deliver the gaseous sample to an analyzer such as an infrared or a Raman gas analyzer (no shown) that provides data from the sample to the PC 217, and the evaluation is conducted as described herein.

The sample gas analyzer or a separate gas analyzer may be optionally employed to determine the bicarbonate concentration in the arterial blood of the patient, as described above. Such option is depicted schematically in FIG. 12, wherein a blood gas analyzer or monitor 250 is provided, with its data output signal being interfaced with the processing system 217. Such blood gas analyzer continuously monitors the patient's intra arterial $pCO_2$, pH, $pO_2$, or other parameters of interest by way of a sensor, such as a fiberoptic sensor placed into the patient's artery. Examples of commercial available blood gas analyzers and sensor components include those marketed by Puritan-Bennett (PB 3300, see Lundsen, T. et al., *J. Clin. Monit.* 10:59–66 (1994), herein incorporated by reference) or by Biomedical Sensors Ltd. (Pfizer)).

These systems (providing continuous arterial $pCO_2$, pH, and bicarbonate values) can also be interfaced into the tonometric $pCO_2$ systems using infrared or Raman spectroscopy technology (discussed herein) to provide an actual value of intramucosal pH, as well as $pCO_2$-gap and pH-gap measurements each time a tonometer $pCO_2$ or $pO_2$ measurement is taken, thus providing more timely trend values for these parameters. This greatly facilitates interpretation of these measurements, since regional (tonometer $pCO_2$ and intramucosal pH) and systemic (arterial $pCO_2$ and pH) can be compared rapidly and directly. It should further be noted that such an optional blood gas monitoring/analyzing interface can be advantageously employed whether liquid or gaseous tonometric sampling is used.

It has also been discovered that the pH of venous blood provides an excellent measure of the adequacy of tissue oxygenation of the whole body or organs, including solid organs, comparable to that achieved in hollow viscus organs by the method described herein, as well as that described in the above-mentioned, commonly-assigned applications that relate to the use of a tonometric catheter to determine the adequacy of tissue oxygenation via the measurement of the pH of the wall of a hollow, viscus organ.

In numerous clinical settings it is now common to monitor the carbon dioxide concentration of the arterial blood of patients, particularly those who are critically ill or under anesthesia; this measurement has been determined to bear a usually predictable relationship to intramucosal pH. One of the most common non-invasive techniques for measuring arterial $CO_2$ is doing so indirectly by measuring the $CO_2$ concentration of the last gas expired from a patient (so called "end-tidal") during normal respiration. The arterial $CO_2$ concentration is then calculated by employing the known correlation between the end-tidal $pCO_2$ and $pCO_2$ of the arterial blood.

It has been discovered in another aspect of the present invention that end-tidal $CO_2$ (as well as the underlying correlation between end-tidal $CO_2$ and the $pCO_2$ of arterial blood) may also be useful in making clinical determination of the condition of an organ of interest when the end-tidal $CO_2$ is compared and contrasted with the $pCO_2$ of air aspirated from a tonometric catheter having a walled sampling chamber inserted into an organ of interest. These measurements having the added convenience of both being measurable by IR or Raman gas analyzers.

However, in order to fully appreciate this, a detailed understanding of the general tonometric method is useful. This background is helpful primarily for the skilled artisan to fully appreciate the relationship of moving from the general tonometric method (which employs $pCO_2$ associated with the wall of the organ of interest and the bicarbonate concentrations of arterial blood) to even more indirect but useful measurements.

In accordance with one preferred embodiment of the present invention, the condition of an organ of interest is determined in a patient in need of such determination when the $pCO_2$ associated with the wall of the organ of interest is sampled and compared to substantially contemporaneous arterial or venous $pCO_2$ values or, in a highly preferred embodiment, end-tidal $pCO_2$ value(s); the $pCO_2$ of the wall of the organ may also be compared to: venous or arterial $pCO_2$ or pH; mixed venous bicarbonate values; transcutaneous $pCO_2$; arterial oxygenation (saturation), arterial $pO_2$, umbilical blood gases, capillary blood gases, and the like.

While not intending to be bound by theory, the following is offered to put these aspects and embodiments of the present invention in proper context.

The assumptions upon which the indirect measurement of intramucosal pH (pHi) are based are valid in normally perfused tissues. In these circumstances, the indirect measurement of intramucosal pH is identical to that measured directly in the submucosal space with a microprobe.

The indirect measurement of intramucosal pH falls in parallel with the pH made directly in the submucosal space when an intramucosal acidosis is induced by endotoxemia, low-flow or no-flow. In those circumstances in which the intramucosal acidosis in induced by endotoxin and flow to the gut is maintained at control levels the measurements are in close agreement (r=0.945). When induced by low-flow and especially no-flow the indirect measurements underestimate the severity of acidosis present in the submucosal space. The disparity between indirect and direct measurements observed in low-flow and no-flow states disappears when blood flow is reestablished and the pH is allowed to return towards normality. Inspection of the twenty-minute values obtained in Antonsson et al's study reveals that the degree of dissociation observed between indirect and direct measurements is a linear function of the rate of change in intramucosal pH induced.

An additional primary assumption upon which the validity of the tonometri- measurement of the adequacy of tissue oxygenation is that the bicarbonate concentration in tissue fluid is the same as that being delivered to it in arterial blood. It has been postulated that the dissociation between calculated and measured pH in low-flow and especially no-flow states may be due to a dissociation between arterial and interstitial bicarbonate induced by the buffering of metabolic acids by tissue bicarbonate.

The hypothesis does not account for the law of mass action which dictates that the fall in bicarbonate intramucosal pH after an intravenous bolus bicarbonate or sudden changes in ventilation regimes.

It is therefore suggested that the primary assumption upon which tonometric measurement of intramucosal pH is based, namely that the tissue bicarbonate is the same as that in arterial blood, is valid in many relevant clinical settings, including those in which the dissociation between measured and calculated intramucosal pH was greatest. The indirect measurement of intramucosal pH appears to be an accurate measure of the pH in interstitial fluid in the most superficial layers of the intestinal mucosa especially in those circumstances in which the measurement is of greatest value, namely patients who appear by all conventional criteria to be adequately resuscitated. The only circumstance in which the measurement might be inaccurate for an extended period is a no-flow state. In this circumstance, the indirect measurement is so abnormal that the presence of the intramucosal acidosis should not be missed even if there is a large discrepancy between actual and assumed measurements. Transient inaccuracies may be expected following an intravenous bolus of bicarbonate or sudden change in pulmonary ventilation.

STOICHIOMETRIC ANALYSIS OF DETERMINANTS OF TISSUE ACIDOSIS

During aerobic metabolism the pH of tissue fluid is determined by the bicarbonate concentration in tissue fluid, the $CO_2$ released by oxidative phosphorylation, and the balance between ATP hydrolysis and resynthesis. In gastric glands the intracellular pH is the same as the extracellular pH in acidotic states. The pH of the extracellular fluid (ECF) is determined by the amount of metabolic acid present and the ability of the ECF to buffer the acid. The $pCO_2$ attained following the buffering of a volatile ($H_2CO_3$ from oxidative phosphorylation) or fixed acid load (protons from ATP hydrolysis) in a closed system, such as the ECF, may be calculated in the manner described by Gattinoni and Feriani.

In normoxic tissues 6 mmol of $CO_2$ are produced for every mmol of glucose consumed in the generation of 38 mmol ATP. 13.5% of a volatile carbonic acid load added to ECF remains after being buffered by proteins and determines the $pCO_2$ present in the ECF. Assuming that the bicarbonate concentration in ECF is 25 mEq/l the metabolism of one mM glucose gives rise to a $pCO_2$ of 27 mmHg (6×0.135/0.03). In normoxic and resting healthy subjects with a tissue bicarbonate of 25 mEq/l the $pCO_2$, determined tonometrically, is 40 mmHg and the intramucosal pH 7.40. If it is assumed that the protons released by ATP hydrolysis are exactly balanced by the protons consumed by ATP resynthesis in oxidative phosphorylation then the aerobic metabolism of 1.48 mM glucose is required to generate the volatile carbonic acid necessary to attain the $pCO_2$ of 40 mmHg (27×1.48=40 mmHg) and pH of 7.40 found in normoxic ECF when the tissue bicarbonate concentration is 25 mEq/l. The $pCO_2$ attained from the buffering of the volatile acids released into normoxic ECF in a tissue bed should increase as the metabolic rate increases, the increased demand for oxygen in the absence of replenishment by flowing blood being met exclusively by an increase in oxygen extraction ratio. A rise in metabolic rate of the magnitude seen in an exercising athlete, which may be as great as 900%, can be expected to cause a rise in equilibrium $pCO_2$ and hence fall in intramucosal pH in normoxic tissues. The magnitude of the fall in pH induced by the rise in $pCO_2$ is offset by the rise in tissue bicarbonate also induced by the buffering of carbonic acid (a volatile acid). The rise in metabolic rate observed in the critically ill is a fraction of that seen in an exercising athlete. Furthermore the oxygen extraction ratio is unchanged and more often decreased in septic patients who exhibit the highest metabolic rate in the critically ill. In any event, the increased metabolic demand for oxygen in the critically ill, especially in those who are septic, is primarily met by an increase in oxygen delivery, oxygen delivery being "demand-dependent" in these circumstances. The $pCO_2$ attained by the buffering of the volatile acid load generated in normoxic ECF should not, therefore, be significantly influenced by changes in metabolic rate of the order encountered in the critically ill.

Aerobic glycolysis and associated generation of $CO_2$ by oxidative phosphorylation decreases in dysoxic states as the availability of oxygen relative to demand decreases. Thus the fall in tissue pH in severely dysoxic states is due almost exclusively to the protons released by adenine nucleotide hydrolysis and their interaction with the body buffers.

If it is assumed that the intramucosal $pCO_2$ and pH are solely determined by the amount of volatile and fixed metabolic acid being buffered in the ECF at the time, the intramucosal pH can be expected to remain constant as oxygen delivery is reduced with or without a reduction in blood flow until the point at which supply-dependency or dysoxia develops. Below this point the $pCO_2$ in ECF should rise and the intramucosal pH fall as the contributions by aerobic metabolism to volatile acid decreases and by anaerobic metabolism to proton release increases with further reductions in oxygen delivery.

Intramucosal pH

The buffering of the protons by tissue bicarbonate in dysoxic states causes the $pCO_2$ to rise. As the bicarbonate concentrations in a "closed system", such as the ECF, is not significantly reduced by the addition of a fixed acid load, the fall in pH must be inversely related to the rise in log $pCO_2$ at any given concentration of tissue bicarbonate. The constant bicarbonate line at 25 mEq/l on a pH–log $pCO_2$ diagram will show that the $pCO_2$ in normoxic ECF at a point A to be 40 mmHg and the pH to be 7.40. The bicarbonate line moves to the right as the equilibrium $pCO_2$ rises above 40 mmHg to a point B in dysoxic states and the tissue pH falls below 7.40. The pH in the dysoxic state may be determined by extrapolation from the $pCO_2$ intercept on the constant bicarbonate line at 25 mEq/l.

The fall in pH induced by dysoxia alone in a tissue with a known bicarbonate concentration may be computed from the difference between the pH in the normoxic and dysoxic states determined from the same constant bicarbonate line (pH-gap), log of the ratio $p_iCO_2/p_aCO_2$ (B–A) or their antilog equivalents ($pCO_2$-gap and $H^+$-gap). It will be appreciated that $pCO_2$-gap is defined as $pCO_2$-gap=$p_iCO_2$–$p_aCO_2$, and $H^+$-gap=$H_a^+$–$H_i^+$. These determinations of the magnitude in fall in pH induced by dysoxia are all dependent upon the assumption that the bicarbonate concentration in the dysoxic ECF is the same as that present in normoxic ECF. If it is assumed that the $pCO_2$ in normoxic ECF is the same as that in arterial blood ($p_aCO_2$) and the tissue $pCO_2$ in dysoxic ECF is the same as the intramucosal $pCO_2$ measured from the lumen of the gut with a walled sampling chamber tonometer ($p_iCO_2$) then the actual pH in dysoxic ECF may be calculated from the following formula (with $pH_a$=pH of arterial blood):

Intramucosal pH=$pH_a$–(log $p_iCO_2$–log $p_aCO_2$)

$\phi$=$pH_a$–log $p_iCO_2/p_aCO_2$ and displayed in a perceptible form, such as human readable or audible form, or machine readable form. Thus, by relating the differences between measured values, wherein the term "difference" does not necessarily mean an arithmetic difference, but refers generally to a comparison of measurements, for example by employing functions and formulas, important biological information may be obtained.

CLINICAL IMPLICATIONS

The indirect measurement of intramucosal pH provides an accurate diagnostic test for the presence of macroscopic and clinical evidence of gastric, small intestinal and large intestinal ischemia in patients. The sensitivity of the intramucosal pH as a diagnostic test for gastric ischemia in man is reported to be 95% and the specificity 100%. For severe ischemic colitis after abdominal aortic surgery the sensitivity is reported to be 100% and the specificity 87%. Of particular relevance to patients who are critically ill is the inability of those with an intramucosal acidosis to secrete acid in response to pentagastrin. Those patients who have a normal gastric intramucosal pH secrete acid in response to this stimulus. It has been suggested that the inability to secrete acid in patients with an intramucosal acidosis may be due to an energy deficit secondary to a dysoxic state. An energy deficit is a known cause of stress ulceration in animals and an impairment of gastric mucosal oxygenation the likely cause of stress ulceration in patients.

The gastric intramucosal pH, measured following the administration of an $H_2$-receptor antagonist to avoid confounding influence of the back diffusion of acid and/or $CO_2$, is inversely related to the hepatic venous lactate concentrations in patients having cardiac surgery (r=–0.71) and correlates closely with this and other indices of splanchnic tissue oxygenation (r=0.92). The gastric intramucosal pH provides, therefore, an index of the adequacy of splanchnic tissue oxygenation.

The gastric intramucosal pH correlates very well and inversely with systemic blood lactate when it is abnormally elevated. In many circumstances, however, blood lactate is normal when the intramucosal pH is low and no correlation between the variables can be demonstrated. Indeed a fall in gastric intramucosal pH may precede a rise in blood lactate in a deteriorating patient by many hours or even days. Changes in intramucosal pH influence the pH dependent enzymes regulating carrier mediated afflux of lactate from muscle and the pH dependent enzyme phosphofructokinase which regulates the rate of anaerobic glycolysis. In addition blood lactate is the net effect of both production by anaerobic glycolysis and consumption by tissues such as the myocardium. The overall correlation between the two variables is thus rather poor (r=–0.40) but nevertheless statistically significant (p=0.026). Thus in addition to providing indices of gastric mucosal and splanchnic tissue oxygenation the indirect measurement of gastric intramucosal pH provides an index of the adequacy of global tissue oxygenation.

The indirect measurement of intramucosal pH provides a measure of the adequacy of tissue oxygenation in the most superficial layer of the mucosa, a region of the gut rendered relatively hypoxic by the counter current exchange system within the mucosal vasculature and hence especially sensitive to alterations in the adequacy of tissue oxygenation. It also provides a measure of the adequacy of tissue oxygenation in a region of the body that is among the first to develop an inadequacy of tissue oxygenation or dysoxia in shock and the last to be restored to normality with resuscitation. Splanchnic vasculature is selectively constricted by the endogenous vasoconstrictors released in shock. For these reasons a fall in intramucosal pH may occur hours to days in advance of any other conventional evidence of an inadequacy of tissue oxygenation, most specifically arterial acidosis, elevation in blood lactate, hypotension and oliguria.

It is concluded that the indirect measurement of gastric intramucosal pH provides a sensitive measure of the adequacy of splanchnic and even global tissue oxygenation in patients in addition to providing an index of the adequacy of superficial gastric mucosal oxygenation.

Correlations with Acid-base Balance and Clinical Events

The indirect measurement of gastric intramucosal pH may correlate very closely with the arterial pH (r=0.67) and other systemic indices of a disturbance in acid-base balance such as arterial bicarbonate (r=0.50), the base deficit in extracellular fluid (r=0.60) and base deficit in blood (r=0.63). This is consistent with the deduction that gastric intramucosal pH provides an index of the balance between the protons released by ATP hydrolysis and consumed in the resynthesis of ATP by oxidative phosphorylation. As with global measurements of blood lactate changes in systemic acid-base balance provide a very dampened signal of disturbances in the adequacy of tissue oxygenation. A fall in intramucosal pH will often precede a fall in arterial pH by hours or even days.

The predictive value of measurements of gastric intramucosal pH for outcome are superior to those of the systemic measures of acid-base balance. Maynard et al, for example, compared the predictive value of measurement of gastric intramucosal pH with those of arterial pH and base excess for death in ICU patients. The likelihood ratio for intramucosal pH was 2.32, for arterial pH 1.52 and base excess 1.47. Logistic regression showed only intramucosal pH to independently predict outcome. In Boyd et al's study, the gastric intramucosal pH was likewise of better predictive value for outcome than base excess. Clinical experience has shown that changes in gastric intramucosal pH correlate far better with the passage of clinical events than either the arterial pH or base excess. Indeed abnormalities in these systemic measures of acid-base imbalance will often occur only as the intramucosal acidosis is being reversed and the patient's condition is improving.

Reperfusion after the low-flow and particularly no-flow states induced in Antonsson et al's validation study in pigs caused the intramucosal pH to rise and the arterial bicarbonate to fall. Similarly in patients the reversal of a severe intramucosal acidosis may be accompanied by a fall in arterial pH and base excess of abnormally low levels. These observations are consistent with the consequences described above of reestablishing perfusion in a dysoxic tissue bed in patients. The $pCO_2$ in the venous effluent leaving the dysoxic tissue bed is elevated but the bicarbonate concentration is not significantly reduced by the buffering of the fixed acid in the tissue bed. The bicarbonate is only reduced by the loss of $CO_2$ during the passage of the venous effluent through the pulmonary circulation (an open system). As dissociation between the direction of change in the intramucosal and systemic pH is to be expected after flow is reestablished through a dysoxic tissue bed.

Intramucosal DH as a Therapeutic Target

"Gut-directed" and "intramucosal pH-directed" therapies may improve outcome. These therapies use a normal intramucosal pH or intramucosal pH greater than 7.35 as an additional therapeutic goal in the resuscitation of patients. This pH was chosen to ensure the pH was maintained well within the normal limits reported for normal subjects. The normal limits may, however, differ from institution to institution with the use of saline and different blood gas analyzers, a problem solved by the air sampling medium (IR or Raman $pCO_2$) analysis embodiments of the present invention. It is furthermore possible that an end-point other than 7.35 might be more appropriate. Values such as 7.25; 7.30; 7.35; 7.37 etc. may also be useful.

While it is clearly desirable to maintain a normoxic state by maintaining the pH-gap at zero, it is not necessarily desirable to maintain the pHi at normal levels. There is a considerable body of evidence indicating that mild degrees of cellular acidosis protect cells in anoxia and ischemia possibly by limiting the activity of the autolytic enzymes responsible for cell injury and death. A cellular acidosis may in addition facilitate carrier-mediated afflux of lactate from cells and bring the intracellular pH to an optimal range for anaerobic glycolysis during anaerobic metabolism. Furthermore the addition of bicarbonate to the extracellular environment attenuates the fall in intracellular pH during ATP depletion and accelerates cell death. The presence of an actual intramucosal acidosis may, therefore, be desirable and efforts to correct a metabolic acidosis with bicarbonate potentially harmful. Indeed the practice of correcting a metabolic acidosis induced by a cardiac arrest by the administration of bicarbonate is no longer recommended.

It is concluded that acid-base balance is intimately related to the adequacy of tissue oxygenation in so far as it relates to the balance between the protons released by ATP hydrolysis and consumed by ATP synthesis from oxidative phosphorylation. The intramucosal DH is determined by the $pCO_2$ attained following and buffering of the metabolic acid released into the ECF and the bicarbonate concentration in ECF at the time—the "buffer hypothesis". The intramucosal pH is related to blood flow only in so far as it relates to the adequacy of tissue oxygenation. The assumption that tissue bicarbonate is the same as that in arterial bicarbonate is only valid in the absence of the generation of an alkaline tide and associated secretion of acid. The indirect measurement of gastric intramucosal pH is the sum of the effects of several determinants of an intramucosal acidosis. It is relevant to activity of pH-dependent enzymes especially as they might relate to cellular injury in dysoxic states. By eliminating the confounding effects of disturbances in systemic acid-base balance the pH-gap provides a measure of the acidosis attributable to an imbalance between ATP hydrolysis and resynthesis, or degree of dysoxia present. Systemic measures of acid-base balance may be dissociated from the adequacy of tissue oxygenation upon reperfusion of a dysoxic tissue bed and correlate poorly with clinical events relative to the measurement of gastric intramucosal pH.

In light of all the above, it will be appreciated that one series of embodiments of the present methods relate to the use of arterial carbon dioxide concentrations (measured directly or indirectly, preferably as an end-tidal carbon dioxide value) as a predictive indicator of the pH of the most superficial layer of the mucosa of the wall of an internal solid organ, particularly the gut. In recognizing that $$pHi = pH_a + \log\frac{p_a CO_2}{p_i CO_2}$$

and that $p_a CO_2$ is approximately equal to $pCO_{2\text{-end tidal}}$, thus $$pHi = pH_a + \log\frac{pCO_{2\text{-end tidal}}}{p_i CO_2}$$

Either or both of these may be employed.

In accordance with the practice of the methods of the present invention, the $pCO_2$ of the wall of the organ is determined. This is preferably done by inserting a tonometric catheter with a walled sampling chamber into or adjacent the organ of interest. The sampling chamber is filled with a gaseous or liquid sampling medium such as air or saline. The sampling medium is allowed to come to equilibrium (equilibrate) with the area so that the $pCO_2$ concentration of the sampling medium reflects the $pCO_2$ of the superficial layer of the mucosa of the organ of interest. The $pCO_2$ concentration of the sampling medium is determined, giving $p_tCO_2$.

In conjunction with the determination of the $pCO_2$ of the mucosa, the carbon dioxide concentration in arterial ($p_aCO_2$) or venous blood is determined directly or indirectly. (A highly preferred indirect measure is end-tidal $pCO_2$, or $pCO_{2\text{-end tidal}}$). The two values (e.g., $p_aCO_2$ and $p_tCO_2$) are then subjected to a nomogram, such as those described in equations above, to determine for example, a pHi value or pH-gap. The time integrated pH-gap can be used as a parameter for assessing the cumulative effects of tissue damage over time. The time differentiated $p_tCO_2$ can be used as a parameter to determine the rate and direction of change in $p_tCO_2$ which may be useful in situations when $p_tCO_2$ may change rapidly (e.g. ventilation changes during ventilator weaning).

In a highly preferred embodiment, the sampling medium for the walled sampling chamber is air. The air is aspirated to an IR or Raman spectrometer. In combination, the measurement of end-tidal $pCO_2$ is employed as a substitute for the arterial $p_aCO_2$. The end-tidal respiratory air is likewise aspirated to an IR or Raman spectrometer. Both gas analyzing devices are controlled by a microcomputer, which also affects the selected nomogram or nomograms which compare the $pCO_2$ of the wall of the organ (gut) with the end-tidal $pCO_2$ value. The gas analyzing devices may operate on a single channel, or via multiple channels.

Additional detection techniques may be performed on the air aspirated from the patient, either via respiration or from the tonometric walled sampling chamber. For example, IR or Raman analyses may be performed to determine the level of anesthetic gases, such as $N_2O$. The results of the nomogram are displayed on a monitor (not shown) in human or machine readable form.

In a highly preferred embodiment, the operation of one example of an infrared gas analyzer is controlled by a microcomputer. The microcomputer itself is not, by itself, part of the present invention. For this reason and because one skilled in the relevant arts could routinely program a general purpose computer to follow the routines required for this application, the microcomputer will not be described in detail herein. (See the U.S. patents incorporated herein by reference.)

Referring now to FIG. 13A, a gas analyzer or detector 320a is shown in accord with the principles of the present invention. Analyzer 320a is specifically designed to monitor the concentration of carbon dioxide in the exhalations of a medical patient—e.g., a patient being ventilated during a surgical procedure.

The major components of the infrared gas analyzer 320a are a powered unit 322a and a sensor assembly 324a of a transducer head 326a and an airway adapter 328a. The transducer head 326a is connected to the unit 322a of the gas analyzer 320a by a conventional electrical cable 330a.

In the application of the invention depicted in FIG. 13A, the gas analyzer 320a is employed to measure fluid parameters of interest, similar to the apparatuses shown and discussed above, except that a gaseous sampling medium, such as air, is conveyed, either manually or automatically, as shown above, and analyzed by the infrared sensor assembly 324a, where the sampling medium is conveyed to the assembly 324a via one of the above described tonometric catheter devices. This information can be effectively employed by medical personnel to monitor the condition of a patient's internal organ more accurately and more quickly than before.

FIG. 13A depicts an in-stream type of infrared gas analyzer, shown merely for purposes of illustration, but one skilled in the art will appreciate that the same principles apply to the use of a side-stream type IR gas analyzer, such as that shown in FIG. 13B.

FIG. 13B depicts a side-stream infrared gas analyzer, similar to that of FIG. 13A, except that the infrared sensor is located inside the powered unit 322b. Also, sampling line 331b is used to convey a continuous gaseous sample from the patient by way of an airway adapter 333b. The gaseous sample is conveyed from the sampling line 331b through a water trap 335b (in order to remove condensate) to the sensor located in the powered unit 322b.

Figure 13C:
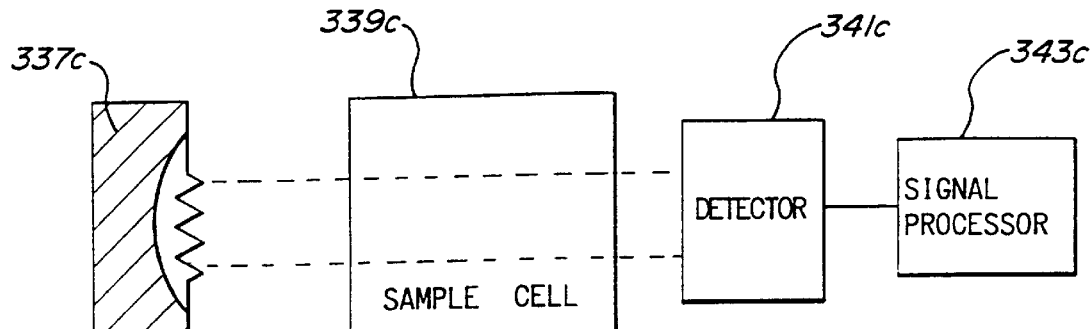
FIG. 13C is a diagrammatic representation of an infrared sensor apparatus usable with the system of either FIG. 13A or FIG. 13B.

FIG. 13C schematically depicts an infrared sensor, which can be used in the infrared sensor assembly 324a of FIG. 13A, or in the powered unit 322b of FIG. 13B. In FIG. 13C, an infrared light source 337c directs an infrared beam through a gas sample cell 339c (located in sensor assembly 324a of FIG. 13A, or in powered unit 322b of FIG. 13B), which contains the gas sample, to a detector 341c, which directs its output signal to a signal processor 343c.

It will be appreciated that Raman spectrometers (gas analyzers) offer advantages over IR analyzers and may be employed in the present invention. A Raman spectrometer is outlined and discussed in Westenskow, D. R., et al., *Anesthesiology* 70:350–355 (1989) and Westenskow, D. R. et al., *Biomed. Inst. & Technol.* November/December:485–489 (1989), herein incorporated by reference. It will also be appreciated that a multichannel Raman in combination with multiple catheters is also contemplated by the present invention. See Niemczyk, T. M. et al., *Laser Focus World* March:85–98 (1993), herein incorporated by reference. The use of the combination of a tonometric catheter and a Raman spectrometer allow the measurement of oxygen gas; nitrogen gas; water; $N_2O$ and other anesthetic agents such as halothane, enflurane, isoflurane and sevoflurane, all of which exhibit Raman scattering. Raman devices not only measure $pCO_2$ more accurately, but can measure $N_2$, $O_2$ and $H_2O$ directly. This may reduce the potential error associated with certain IR techniques, especially where other substances ($N_2O$; $O_2$; $H_2O$) may effect the IR $pCO_2$ measurement due to errors from overlapping wavelengths. The ability to measure $O_2$ directly with a Raman system instead of employing two sensors to measure $O_2$ and $CO_2$ as with the IR system is also important, especially with tonometric samples wherein the volume of sample may not be sufficient for two measurements.

By measuring $O_2$ and $N_2$, air leaks may be detected and detection is highly accurate. For example, equilibrated tonometric samples could be compared to the air concentration of $O_2$ and $N_2$. Any samples that "look like air" to the system would thus be discarded. This may be especially useful in situations where a $pCO_2$ in the stomach is high (e.g. 80 mmHg) and mixing with air during high suction from a nasogastric tube may reduce the $CO_2$ level, but not to zero. In a Raman system, this sample would be detected as an air leak. However, in an IR system an inaccurate $pCO_2$ reading may result because the means for detecting the air leak are based primarily on the $pCO_2$ reading.

Another important advantage of the Raman spectrometer is the ability to employ a fiberoptic probe within the sampling chamber 40 of the tonometric catheter. The fiber optic probe may also be used in combination with the catheter such that the tip of the fiberoptic probe resides inside the balloon of the catheter. This approach allows low or no dead space applications and lends itself to applications where excessive inflation of the balloon is not possible or desirable e.g. colon or stomach of a neonate, within a wound and on surfaces of organs.

The sampling principles used with the Raman spectrometers are similar to those used with side-stream monitors, discussed above, in that a sample is aspirated from the patients respiratory line and analyzed. Thus, to connect a tonometric catheter of the present invention to the Raman spectrometer, a pump to infuse and aspirate the sample may be added. Alternatively, the aspirating pump on the Raman spectrometer may be modified in a manner to allow it to infuse the tonometer balloon (intermittently or continuously), along with its normal function of aspirating samples for respiratory and anesthetic gas measurements. This modified system is shown in FIG. 14.

Figure 14:
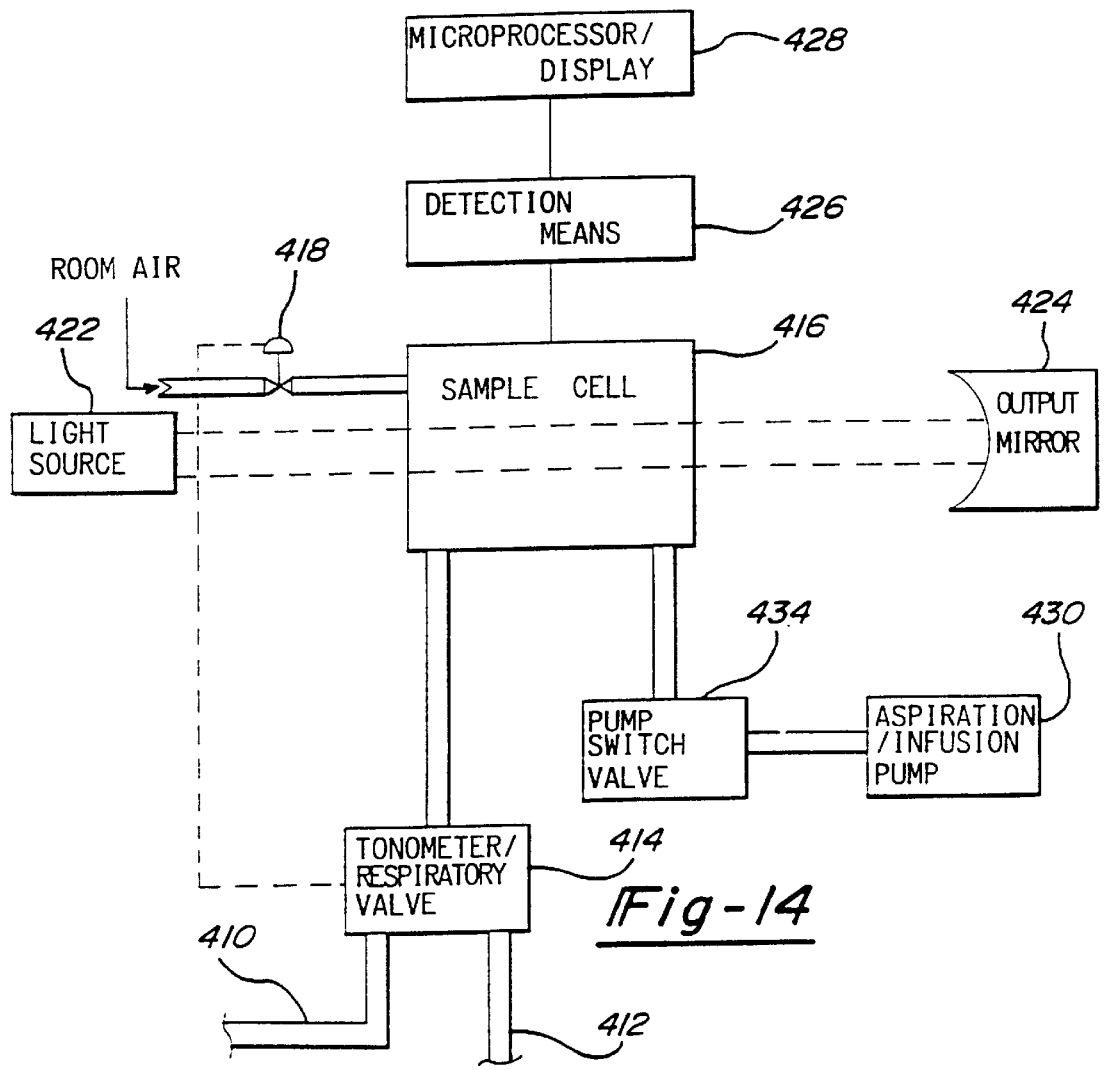
FIG. 14 is a schematic representation of a modified Raman system according to the present invention.

As shown in FIG. 14, a Raman spectrometer may contain a gas sample cell 416 between a light source 422 such as a laser, and an output mirror 424. The Raman scattered light is directed through detection means such as collection optics, filters, focusing optics and detectors, known to those skilled in the art, are depicted collectively at 426 in FIG. 14. A microprocessor and display are generally referred to at 428.

Also shown in FIG. 14, in a preferred system of the present invention employing a Raman spectrometer, a aspiration and infusion pump 430 is in communication with a pump switch valve 434 which controls the incoming and outgoing sample in the sample cell 416. A sample from a tonometric balloon enters the system as shown at 410 and, as shown at 412, a respiratory sample may also enter the system. Both samples then enter a tonometer/respiratory valve 414 that allows either one of the samples to enter the sample cell 416 while excluding the other sample. The sample cell of the Raman spectrometer may be on the order of 5 microliters, much smaller than the 800 microliter cell of a typical IR system, and is therefore easily able to accurately measure even a low volume tonometric sample.

A preferred Raman spectrometer employed in the present invention is the Rascals® II, available from Ohmeda Monitoring Systems, Louisville, Colo. The Rascal® II incorporates a feature that continuously flushes the sample cell with room air to keep the optics of the sample cell clean. Because respiratory gases are continuously sampled at a rate of about 200 ml/min, the typical air flush rate of about 5 ml/min does not impact the accuracy of the measurement. In contrast, a tonometer sample flow may be slower and the sample volume is less and therefore the air flush may impact the accuracy of the measurement. Thus, in a preferred embodiment, this air flush feature may be modified as shown in FIG. 14, to contain an automatic air intake valve 418 wherein the flow of incoming room air may be controlled. The automated air intake valve 418 is in communication with the tonometric/respiratory valve 414 generally through a control interlock (depicted with dashed line) known to those skilled in the art, wherein the automated air intake valve 418 will be open when a respiratory sample is flowing through the tonometer/respiratory valve 414, and closed when a tonometric sample is flowing through the valve 414.

It will also be appreciated that with improvements in solid state technology, a laser system may be designed to utilize a Raman spectrometer in a main-stream system. Furthermore, improvements in laser science will result in smaller size lasers and less noise, cost and power consumption.

Figure 15:
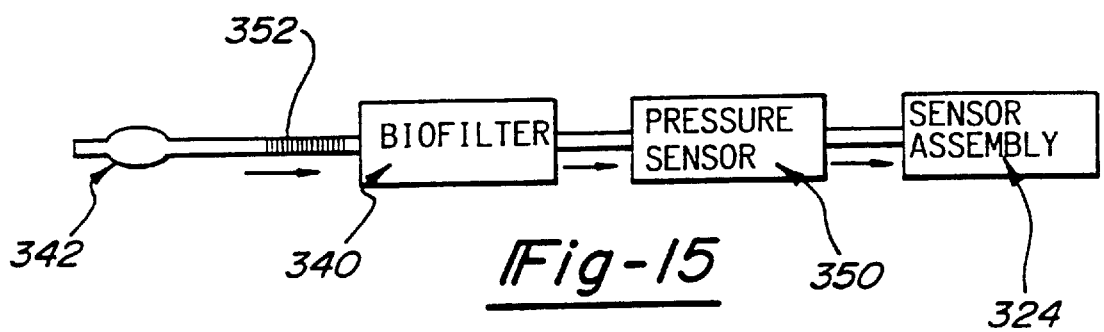
FIG. 15 is a schematic representation of a number of alternate variations on the invention.

FIG. 15 schematically illustrates a biological filter (biofilter) apparatus 340 being employed in-line, between an exemplary tonometric catheter apparatus 342 and the above-discussed exemplary infrared or Raman sensor assembly 324 for filtering out undesirable contaminants. The bio-filter 340 can be any of a number of biological filters known to those skilled in the art and is especially useful to allow side-stream systems to allow sample return or in-stream infrared gas analyzer apparatuses to be used in multi-patient applications. An example of a suitable biofilter for this purpose is a Dualex™ 0.2 micron filter unit, SLFG 025 XS, manufactured by Millipore Corporation, Bedford, Massachusetts.

Due to the sensitivity of the current commercial infrared sensors or detectors to moisture content, and due to the high moisture content of air sampling-medium based $pCO_2$ samples coming from both an in vivo tonometric walled sampling chamber and end-tidal samples, a moisture filter or other dehumidifying means is optionally employed. For example, an air-based $pCO_2$ sample can be passed through dehumidification tubing 352, such as Nafion® polymer tubing, for example. The biofilter 340 and the optional dehumdification tubing 352 can be used with either the infrared sensor systems or the Raman sensor systems described above.

Other methods of eliminating moisture problems include employing a heat sink around part or all of the IR optical path, particularly the lens window where the IR source passes light. Yet another means includes employing a water trap or a barrier or filter which is selectively permeable to water vapor (moisture) and/or the gases of interest, particularly $pCO_2$.

It should therefore also be noted that the filter 340 can also optionally include a dehumidifying means, e.g., a water vapor filter or removal medium, either alone or in addition to the biological filter, for allowing any water vapor in the sampling medium or the sampling chamber to disperse in the environment by delivering the mixture thereof past a water-vapor-permeable wall or medium.

FIG. 15 also schematically illustrates the addition of a gaseous sampling medium pressure sensor and/or regulator 350 (optional) for measuring the pressure of a gas sampling medium, such as air, for example, and/or for regulating such pressure to be substantially at some predetermined pressure level, such as atmospheric pressure, or example, at which the gas analyzer is designed to operate and give accurate, reliable results.

It will be appreciated that the gaseous sampling medium pressure sensor and/or regulator 350 is capable of recording and processing a pressure signal. Until now there has not been a reliable means for measuring respiration rate when the patient is breathing on their own. However, in accordance with the present invention, small pressure changes induced by the patient's respiration may be derived from the pressure signal to provide signals indicating respiration rate (RR). For example, if the pressure signal resembles a sine curve, wherein the period of the signal is represented by T, then the respiratory rate=1/T.

It should also be noted that any of the embodiments of the sensor assembly 324 can also include other sensors (other than infrared or Raman) for measuring still other parameters. An example would be a paramagnetic $O_2$ sensor or Clark-type polarographic $O_2$ sensor.

Figure 16:
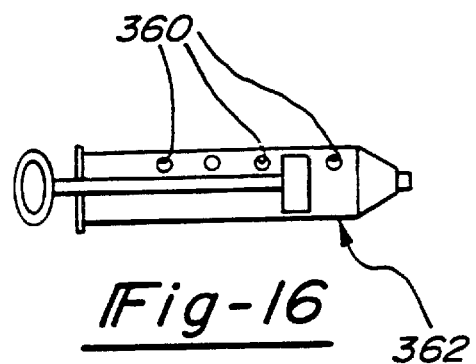
FIG. 16 is a diagrammatic representation of a manual syringe, modified to provide for sample pressure equalization in the present invention.

It will be appreciated that in a manual system, wherein a syringe is used to draw the gaseous sample into the sensor assembly, it has been found to be useful to provide one or more holes 360 in the syringe body 362 shown in FIG. 16 in order to allow for pressure regulation and equalization with the atmosphere or some predetermined pressure level. Alternatively, a pressure-difference caused by a pump, with or without a pressure regulation or connection device, as needed, can be employed. In addition, as is clear from the foregoing discussion, the system can use a single-tube catheter device or a dual-tube version, wherein one tube delivers the sampling medium to the sampling chamber and the other is used to extract it for measurement.

The gas analyzers described herein, may also be modified in preferred embodiments to make automated regular intermittent or continuous measurements of $pCO_2$ by way of a tonometric catheter. An automated pumping system may be utilized to withdraw (intermittently or continuously) the sample and purge the system. A pressure sensor, such as that described above, must be available to correct for measuring chamber pressure and to detect balloon inflation and deflation. It will be appreciated that the gas analyzers will be in communication with a computer or other peripheral equipment, such as a recorder and interfaced by standard procedures. The analyzers may be programmed, for example, through the computer to automatically measure and calculate desired values. For example, in preferred embodiments, three modes of operation are available and may be selected from a menu via the computer keypad. The following is a description of each mode:

MODE 1: Intramucosal $pCO_2$ Mode (Default Mode).

The instrument automatically determines tonometer intramucosal $pCO_2$ ($p_iCO_2$) at pre-set intervals (e.g. every 5 mim). A digital display and trend of $p_iCO_2$ may be displayed.

If arterial $pCO_2$ ($p_aCO_2$) is entered manually via the keypad, a pH-gap, defined as pH-gap=(arterial pH−intramucosal pH), will be calculated. The pH-gap will be based on the $p_iCO_2$ at the time $p_aCO_2$ was measured. A pH-gap trend may be displayed graphically. The $p_iCO_2$ trend display may also display $p_aCO_2$.

If $p_aCO_2$ and arterial pH ($pH_a$) are both entered, the intramucosal pH (pHi) will be calculated. The pHi will be based on the $p_iCO_2$ at the time the $p_aCO_2$ and $pH_a$ were measured. A pHi trend may be displayed graphically.

Respiratory rate is calculated from the measured pressure in the balloon with an in-line pressure sensor described above, and may be displayed digitally and as a trend.

MODE 2: Dual Operation Mode.

In this mode, end-tidal $CO_2$ ($EtCO_2$) is monitored continuously, except when interrupted during each $p_iCO_2$ cycle (e.g. approximately 1 min at 5 min intervals). Intramucosal $pCO_2$ and $EtCO_2$ may be displayed as two superimposed trend curves.

If arterial $pCO_2$ ($p_aCO_2$) is entered manually via the keypad, a pH-gap, will be calculated. The pH-gap will be based on the $p_iCO_2$ at the time $p_aCO_2$ was measured. A pH-gap trend may be displayed graphically. The $p_iCO_2$ trend display may also display $p_aCO_2$.

If $p_aCO_2$ and arterial pH ($pH_a$) are both entered, the intramucosal pH (pHi) will be calculated. The pHi will be based on the $p_iCO_2$ at the time the $p_aCO_2$ and $PH_a$ were measured. The pHi may be displayed graphically.

MODE 3: End-Tidal $CO_2$ ($EtCO_2$).

The system may also function as a normal $EtCO_2$ monitor.

It will be appreciated that alarm systems notifying the user of various abnormal conditions may also be employed in conjunction with the above system. It will further be appreciated that variables such as body temperature of the patient, catheter type and elapsed time since blood gas withdrawal, may also be entered through the keyboard to allow for greater accuracy in measurements and thus greater accuracy in calculated values and trends. Also, an alternative to manually entering the temperature, it may optionally be measured by measuring the temperature of the air sample withdrawn from the tonometric catheter or with a thermistor in the balloon, and displayed.

Accordingly, while several preferred embodiments of the invention have been disclosed, it will be appreciated that principles of the invention, as set forth in the following claims, are applicable to other embodiments.

What is claimed is:

1. An integral tonometric catheter apparatus for measuring a liquid fluid or gaseous fluid property indicative of the condition of an organ of the body of a human or other mammal in vivo, comprising:

(a) a flexible elongated tonometric catheter tube having at least one lumen extending longitudinally therethrough;

(b) at least one sampling chamber on said catheter tube for receiving, containing, and discharging a gaseous sampling medium, said sampling chamber having a wall and being in fluid communication with the interior of said at least one lumen, said sampling chamber generally surrounding a portion of said catheter tube and being sealingly interconnected therewith, at least a portion of the wall of said sampling chamber being composed of a wall material that is selectively permeable to one or more liquid fluids or gaseous fluids of interest, said wall material being substantially impermeable to other liquid fluids or gaseous fluids present in the organ, said sampling chamber being suitable for being placed in the organ of the human or other mammal and said sampling chamber forming an interior space with said catheter tube in order to allow one or more liquid fluids or gaseous fluids of interest from the tissue of the wall portion of the organ to permeate into said sampling chamber and to be received by said sampling medium, said catheter tube extending to a position outside of the body of the human or other mammal, said catheter tube being composed of a material that is substantially impermeable to the gaseous or liquid fluids of interest, and said at least one lumen providing fluid communication between said sampling chamber and the outside of the body of the human or other mammal for the gaseous sampling medium to flow therebetween;

(c) infrared sensor means for sensing the level of at least one of said liquid fluids or gaseous fluids of interest permeated from the tissue of the wall portion of the organ to said gaseous sampling medium in said sampling chamber;

(d) means for direct fluid communication between said sampling chamber and said infrared sensor means; and (e) means providing a gaseous sampling medium to said at least one lumen of said catheter tube for supply to said sampling chamber, said means removing the gaseous sampling medium and the received one or more liquid or gaseous fluids of interest from the sampling chamber and supplying same to said infrared sensor means.

2. An apparatus according to claim 1, wherein said walled sampling chamber is defined by a balloon member generally surrounding a portion of said catheter tube and sealingly interconnected therewith, the wall of said balloon member being composed of said wall material that is permeable to said one or more liquid fluids or gaseous fluids of interest and substantially impermeable to other liquid fluids or gaseous fluids, said balloon member being deformable for forming said interior space with said catheter tube.

3. An apparatus according to claim 1, wherein said infrared sensor means includes a non-dispersive infrared spectrophotometry device of the in-stream type for measuring said liquid fluids or gaseous fluids of interest.

4. An apparatus according to claim 1, wherein said infrared sensor means includes a non-dispersive infrared spectrophotometry device of the side-stream type for measuring said liquid fluids or gaseous fluids of interest.

5. An apparatus according to claim 1, further including a bio-filtering means in said catheter tube between said walled sampling chamber and said infrared sensor for filtering out undesirable contaminants.

6. An apparatus according to claim 1, wherein said sampling chamber is further defined as a sampling chamber for receiving, containing, and discharging a gaseous sampling medium comprising air.

7. An apparatus according to claim 1, further including sample pressure sensing means operatively associated with one of said catheter or direct fluid communication means for sensing the pressure of said gaseous sampling medium.

8. An apparatus according to claim 7, further including pressure regulation means operatively associated with one of said catheter or direct fluid communication means for regulating the pressure of said gaseous sampling medium generally at a predetermined pressure level.

9. An apparatus according to claim 8, wherein said pressure regulation means is further defined as regulating the pressure of the gaseous sampling medium to substantially atmospheric pressure.

10. An apparatus according to claim 1, wherein said sampling chamber is defined by an opening in said catheter tube communicating with said at least one lumen, said opening being covered by said wall material sealingly interconnected with said catheter tube substantially adjacent said opening.

11. An apparatus according to claim 10, wherein said wall material is deformable.

12. An apparatus according to claim 1, further including temperature sensing means for sensing a core temperature of the human or other mammal, said temperature sensing means being exposed to said sampling medium.

13. An apparatus according to claim 12, wherein said temperature sensing means is in said sampling chamber.

14. An apparatus according to claim 1, further including pressure sensing means for sensing a respiration rate of the human or other mammal, said pressure sensing means being in fluid communication with said sampling chamber.

15. An apparatus according to claim 14, wherein said pressure sensing means is in said sampling chamber.

16. An integral tonometric catheter apparatus for measuring a liquid fluid or gaseous fluid property indicative of the condition of an organ of the body of a human or other mammal in vivo, comprising:
(a) a flexible elongated tonometric catheter tube having at least one lumen extending longitudinally therethrough;
(b) at least one sampling chamber on said catheter tube for receiving, containing, and discharging a gaseous sample medium, said sampling chamber being in fluid communication with the interior of said at least one lumen, said sampling chamber being defined by a balloon member generally surrounding a portion of said catheter tube and being sealingly interconnected therewith, said balloon member having a wall at least a portion of the wall of said balloon member being composed of a wall material that is selectively permeable to one or more liquid fluids or gaseous fluids of interest, said wall material being substantially impermeable to other liquid fluids or gaseous fluids present in the organ, said balloon member being suitable for being placed in the organ of the human or other mammal, said balloon member being inflatable for forming an interior space between said balloon member and said catheter tube in order to allow said one or more liquid fluids or gaseous fluids of interest from the tissue of the wall portion of the organ to permeate into said sampling chamber and to be received by said sampling medium, said catheter tube extending to a position outside of the body of the human or other mammal, said catheter tube being composed of a material that is substantially impermeable to the gaseous or liquid fluids of interest, and said at least one lumen providing fluid communication between said sampling chamber and the outside of the body of the human or other mammal for a gaseous sampling medium to flow therebetween;
(c) infrared sensor means for sensing the level of at least one of said liquid fluids or gaseous fluids of interest permeated from the tissue of the wall portion of the organ into said gaseous sampling medium in said sampling chamber;
(d) means for direct fluid communication between said sampling chamber and said infrared sensor means; and
(e) means providing a gaseous sampling medium to said at least one lumen of said catheter tube for supply to said balloon member, said means removing the gaseous sampling medium and the received one or more liquid or gaseous fluids of interest from said balloon member supplying same to said infrared sensor means.

17. An apparatus according to claim 16, wherein said infrared sensor means includes a non-dispersive infrared spectrophotometry device of the in-stream type for measuring said liquid fluids or gaseous fluids of interest.

18. An apparatus according to claim 16, wherein said infrared sensor means includes a non-dispersive infrared spectrophotometry device of the side-stream type for measuring of said liquid fluids or gaseous fluids of interest.

19. An apparatus according to claim 16, further including a bio-filtering means in said catheter tube between said walled sampling chamber and said infrared sensor for filtering out undesirable contaminants.

20. An apparatus according to claim 16, wherein said balloon member is further defined as a balloon member for receiving, containing, and discharging a gaseous sampling medium comprising air.

21. An apparatus according to claim 16, further including sample pressure sensing means operatively associated with one of said catheter or direct fluid communication means for sensing the pressure of said gaseous sampling medium.

22. An apparatus according to claim 21, further including pressure regulation means operatively associated with one of said catheter or direct fluid communication means for regulating the pressure of said gaseous sampling medium generally at a predetermined pressure level.

23. An apparatus according to claim 22, wherein said pressure regulation means is further defined as regulating the pressure of the gaseous sampling medium to substantially atmospheric pressure.

24. An apparatus according to claim 16, further including temperature sensing means for sensing a core temperature of the human or other mammal, said temperature sensing means being exposed to said sampling medium.

25. An apparatus according to claim 24, wherein said temperature sensing means is in said sampling chamber.

26. An apparatus according to claim 16, further including pressure sensing means for sensing a respiration rate of the human or other mammal, said pressure sensing means being in fluid communication with said sampling chamber.

27. An apparatus according to claim 26, wherein said pressure sensing means is in said sampling chamber.

28. A method of measuring a liquid fluid or gaseous fluid property indicative of the condition of an organ of the body of a human or other mammal in vivo, comprising the steps of:
 (a) providing a flexible, elongated tonometric catheter tube having at least one lumen extending longitudinally therethrough with at least one sampling chamber on said catheter tube for receiving, containing, and discharging a gaseous sampling medium, said sampling chamber having a wall and being in fluid communication with the interior of said at least one lumen, said sampling chamber generally surrounding a portion of said catheter tube and being sealingly interconnected therewith, the wall of said sampling chamber being composed of a wall material that is selectively permeable to one or more liquid fluids or gaseous fluids of interest that are present in the organ, said wall material being substantially impermeable to other liquid fluids or gaseous fluids that are present in the organ, said sampling chamber defining an interior space between said sampling chamber and said catheter tube, said catheter tube being composed of a material that is substantially impermeable to the gaseous or liquid fluids of interest;
 (b) providing an infrared sensor apparatus for sensing the level of at least one of said liquid fluids or gaseous fluids of interest with direct fluid communication between said sampling chamber and said infrared sensor apparatus via said at least one lumen of said catheter;
 (c) introducing the catheter tube into the organ of interest so that said sampling chamber is disposed at a desired sampling site, said catheter tube extending to a position outside the body of the human or other mammal so that said at least one lumen provides fluid communication between said sampling chamber and the outside of the body of the human or other mammal and by which the direct fluid communication between said sampling chamber and said infrared sensor apparatus is provided;
 (d) introducing a gaseous sampling medium into said catheter tube and into said interior space defined by said sampling chamber and said catheter tube;
 (e) leaving said sampling chamber disposed at said sampling site for a length of time sufficient to allow said liquid fluid or gaseous fluids of interest that are present at said sampling site to diffuse across the wall of the sampling chamber into said gaseous sampling medium contained within said sampling chamber;
 (f) withdrawing at least a portion of said gaseous sampling medium through said catheter tube to said infrared sensor apparatus by means of the direct fluid communication between said sampling chamber and said infrared sensor apparatus; and
 (g) analyzing the sample thus withdrawn using said infrared sensor apparatus to determine the level present of said liquid fluid or gaseous fluid in said withdrawn gaseous sampling medium.

29. A method according to claim 28, wherein the step of providing an infrared sensor apparatus is further defined as providing a non-dispersive infrared spectrophotometry device of the in-stream type for measuring of said liquid fluids or gaseous fluids of interest.

30. A method according to claim 28, wherein the step of providing an infrared sensor apparatus is further defined as providing a non-dispersive infrared spectrophotometry device of the side-stream type for measuring said liquid fluids or gaseous fluids of interest.

31. A method according to claim 28, further including the step of providing a bio-filter device in said catheter tube between said walled sampling chamber and said infrared sensor and filtering said gaseous or liquid sampling medium through said bio-filter prior to analyzing said gaseous sampling medium using said infrared sensor apparatus in order to filter out undesirable contaminants.

32. A method according to claim 28, further including the step of measuring the pressure of said gaseous sampling medium.

33. A method according to claim 32, further including the step of regulating the pressure of said gaseous sampling medium generally at a predetermined pressure level.

34. A method according to claim 33, wherein the step of regulating the pressure to a predetermined pressure level is further defined as regulating the pressure to substantially atmospheric pressure.

35. A method according to claim 28, further including the step of providing a temperature sensing means for sensing a core temperature of the human or other mammal, said temperature sensing means being exposed to said sampling medium.

36. A method according to claim 35, wherein the step of providing a temperature sensing means is further defined as providing a temperature sensing means in said sampling chamber.

37. A method according to claim 28, further including the step of providing a pressure sensing means for sensing a respiration rate of the human or other mammal, said pressure sensing means being provided in fluid communication with said sampling chamber.

38. A method according to claim 37, wherein the step of providing a pressure sensing means is further defined as providing a pressure sensing means in said sampling chamber.

39. A method of measuring a liquid fluid or gaseous fluid property indicative of the condition of an organ of the body of a human or other mammal in vivo comprising the steps of:
 (a) providing a flexible, elongated tonometric catheter tube having at least one lumen extending longitudinally therethrough with at least one sampling chamber on said catheter tube for receiving, containing, and discharging a gaseous sampling medium and being in fluid communication with the interior of said at least one lumen, said walled sampling chamber being defined by a balloon member generally surrounding a portion of said catheter tube and being sealingly interconnected therewith, said balloon member having a wall, the wall of said balloon member being composed of a wall material that is selectively permeable to one or more liquid fluids or gaseous fluids of interest, said wall material being substantially impermeable to other liquid fluids or gaseous fluids, said balloon member defining an interior space between said sampling chamber and said catheter tube, said catheter tube being composed of a material that is substantially impermeable to the gaseous or liquid fluids of interest;
 (b) providing an infrared sensor apparatus for sensing the level of at least one of said liquid fluids or gaseous fluids of interest with direct fluid communication between said sampling chamber and said infrared sensor apparatus via said at least one lumen of said catheter;
 (c) introducing the catheter tube into the organ of interest so that said balloon member is disposed at a desired sampling site, said catheter tube extending to a position outside the body of the human or other mammal so that said lumen provides fluid communication between said balloon member and the outside of the body of the human or other mammal and by which the direct fluid communication between said sampling chamber and said infrared sensor apparatus is provided;

(d) introducing a gaseous sampling medium into said catheter tube and into said interior space defined by said balloon member and said catheter tube;

(e) leaving said sampling chamber disposed at said sampling site for a length of time sufficient to allow said liquid fluids or gaseous fluids of interest that are present at said sampling site to diffuse across the wall of the balloon member into said gaseous sampling medium contained within said balloon member;

(f) withdrawing at least a portion of said gaseous or liquid sampling medium through said catheter tube to said infrared sensor apparatus by means of the direct fluid communication between said sampling chamber and said infrared sensor apparatus; and (g) analyzing the sample thus withdrawn using said infrared sensor means to determine the level present of said liquid fluid or gaseous fluid in said withdrawn gaseous sampling medium.

40. A method according to claim 39, wherein the step of providing an infrared sensor apparatus is further defined as providing a non-dispersive infrared spectrophotometry of the device for in-stream type for measuring said liquid fluids or gaseous fluids of interest.

41. A method according to claim 39, wherein the step of providing an infrared sensor apparatus is further defined as providing a non-dispersive infrared spectrophotometry device of the side-stream type for measuring said liquid fluids or gaseous fluids of interest.

42. A method according to claim 39, further including the step of providing a bio-filter device in said catheter tube between said walled sampling chamber and said infrared sensor and filtering said gaseous or liquid sampling medium through said bio-filter prior to said analyzing gaseous sampling medium using said infrared sensor apparatus in order to filter out undesirable contaminants.

43. A method according to claim 39, further including the step of measuring the pressure of said gaseous sampling medium.

44. A method according to claim 43, further including the step of regulating the pressure of said gaseous sampling medium generally at a predetermined pressure level.

45. A method according to claim 44, wherein the step of regulating the pressure to a predetermined pressure level is further defined as regulating the pressure to substantially atmospheric pressure.

46. A method according to claim 39, further including the step of providing a temperature sensing means for sensing a core temperature of the human or other mammal, said temperature sensing means being exposed to said sampling medium.

47. A method according to claim 46, wherein the step of providing a temperature sensing means is further defined as providing a temperature sensing means in said sampling chamber.

48. A method according to claim 39, further including the step of providing a pressure sensing means for sensing a respiration rate of the human or other mammal, said pressure sensing means being provided in fluid communication with said sampling chamber.

49. A method according to claim 48, wherein the step of Providing a pressure sensing means is further defined as providing a pressure sensing means in said sampling chamber.

50. An integral tonometric catheter apparatus for measuring a liquid fluid or gaseous fluid property indicative of the condition of an organ of the body of a human or other mammal in vivo, comprising:

(a) a flexible elongated tonometric catheter tube having at least one lumen extending longitudinally therethrough;

(b) at least one sampling chamber on said catheter tube for receiving, containing, and discharging a gaseous sampling medium, said sampling chamber having a wall and being in fluid communication with the interior of said at least one lumen, said sampling chamber generally surrounding a portion of said catheter tube and being sealingly interconnected therewith, at least a portion of the wall of said sampling chamber being composed of a wall material that is selectively permeable to one or more liquid fluids or gaseous fluids of interest, said wall material being substantially impermeable to other liquid fluids or gaseous fluids present in the organ, said sampling chamber being suitable for being placed in the organ of the human or other mammal and said sampling chamber forming an interior space with said catheter tube in order to allow one or more liquid fluids or gaseous fluids of interest from the tissue of the wall portion of the organ to permeate into said sampling chamber and to be received by said sampling medium, said catheter tube extending to a position outside of the body of the human or other mammal, said catheter tube being composed of a material that is substantially impermeable to the gaseous or liquid fluids of interest, and said at least one lumen providing fluid communication between said sampling chamber and the outside of the body of the human or other mammal for the gaseous sampling medium to flow therebetween;

(c) Raman sensor means for sensing the level of at least one of said liquid fluids or gaseous fluids of interest permeated from the tissue of the wall portion of the organ to said gaseous sampling medium in sampling chamber;

(d) means for direct fluid communication between said sampling chamber and said Raman sensor means; and (e) means providing a gaseous sampling medium to said at least one lumen of said catheter tube for supply to said sampling chamber, said means removing the gaseous sampling medium and the received one or more liquid or gaseous fluids of interest from the sampling chamber and supplying same to said Raman sensor means.

51. An apparatus according to claim 50, wherein said walled sampling chamber is defined by a balloon member generally surrounding a portion of said catheter tube and sealingly interconnected therewith, the wall of said balloon member being composed of said wall material that is permeable to said one or more liquid fluids or gaseous fluids of interest and substantially impermeable to other liquid fluids or gaseous fluids, said balloon member being deformable for forming said interior space with said catheter tube.

52. An apparatus according to claim 50, wherein said Raman sensor means includes means of the in-stream type for measuring of said liquid fluids or gaseous fluids of interest.

53. An apparatus according to claim 50, wherein said Raman sensor means includes means of the side-stream type for measuring said liquid fluids or gaseous fluids of interest.

54. An apparatus according to claim 50, further including a bio-filtering means in said catheter tube between said walled sampling chamber and said Raman sensor for filtering undersirable contaminants.

55. An apparatus according to claim 50, wherein said sampling chamber is further defined as a sampling chamber for receiving, containing, and discharging a gaseous sampling medium comprising air.

56. An apparatus according to claim 50, further including sample pressure sensing means operatively associated with one of said catheter or direct fluid communication means for sensing the pressure of said gaseous sampling medium.

57. An apparatus according to claim 56, further including pressure regulation means operatively associated with one of said catheter or direct fluid communication means for regulating the pressure of said gaseous sampling medium generally at a predetermined pressure level.

58. An apparatus according to claim 57, wherein said pressure regulation means is further defined as regulating the pressure of the gaseous sampling medium to substantially atmospheric pressure.

59. An apparatus according to claim 50, wherein said sampling chamber is defined by an opening in said catheter tube communicating with said at least one lumen, said opening being covered by said wall material sealingly interconnected with said catheter tube substantially adjacent said opening.

60. An apparatus according to claim 59, wherein said wall material is deformable.

61. An apparatus according to claim 50, further including temperature sensing means for sensing a core temperature of the human or other mammal, said temperature sensing means being exposed to said sampling medium.

62. An apparatus according to claim 61, wherein said temperature sensing means is in said sampling chamber.

63. An apparatus according to claim 50, further including pressure sensing means for sensing a respiration rate or the human or other mammal, said pressure sensing means being in fluid communication with said sampling chamber.

64. An apparatus according to claim 63, wherein said pressure sensing means is in said sampling chamber.

65. An integral tonometric catheter apparatus for measuring a liquid fluid or gaseous fluid property indicative of the condition of an organ of the body of a human or other mammal in vivo, comprising:
(a) a flexible elongated tonometric catheter tube having at least one lumen extending longitudinally therethrough;
(b) at least one sampling chamber on said catheter tube for receiving, containing, and discharging a gaseous sample medium, said sampling chamber being in fluid communication with the interior of said at least one lumen, said sampling chamber being defined by a balloon member generally surrounding a portion of said catheter tube and being sealingly interconnected therewith, said balloon member having a wall, at least a portion of the wall of said balloon member being composed of a wall material that is selectively Permeable to one or more liquid fluids or gaseous fluids of interest, said wall material being substantially impermeable to other liquid fluids or gaseous fluids present in the organ, said balloon member being suitable for being placed in the organ of the human or other mammal, said balloon member being inflatable for forming an interior space between said balloon member and said catheter tube in order to allow said one or more liquid fluids or gaseous fluids of interest from the tissue of the wall portion of the organ to permeate into said sampling chamber and to be received by said sampling medium, said catheter tube extending to a position outside of the body of the human or other mammal, said catheter tube being composed of a material that is substantially impermeable to the gaseous or liquid fluids of interest, and said at least one lumen providing fluid communication between said sampling chamber and the outside of the body of the human or other mammal for a gaseous sampling medium to flow therebetween;
(c) Raman sensor means for sensing the level of at least one of said liquid fluids or gaseous fluids of interest permeated from the tissue of the wall portion of the organ into said gaseous sampling medium in said sampling chamber;
(d) means for direct fluid communication between said sampling chamber and said Raman sensor means; and
(e) means providing a gaseous sampling medium to said at least one lumen of said catheter tube for supply to said balloon member, said means removing the gaseous sampling medium and the received one or more liquid or gaseous fluids of interest from said balloon member and supplying same to said Raman sensor means.

66. An apparatus according to claim 65, wherein said Raman sensor means includes means of the in-stream type for measuring said liquid fluids or gaseous fluids of interest.

67. An apparatus according to claim 65, wherein said Raman sensor means includes means of the side-stream type for measuring of said liquid fluids or gaseous fluids of interest.

68. An apparatus according to claim 65, further including a bio-Liltering means in said catheter tube between said walled sampling chamber and said Raman sensor for filtering out undersirable contaminants.

69. An apparatus according to claim 65, wherein said balloon member is further defined as a balloon member for receiving, containing, and discharging a gaseous sampling medium comprising air.

70. An apparatus according to claim 65, further including sample pressure sensing means operatively associated with one of said catheter or direct fluid communication means for sensing the pressure of said gaseous sampling medium.

71. An apparatus according to claim 70, further including pressure regulation means operatively associated with one of said catheter or direct fluid communication means for regulating the pressure of said gaseous sampling medium generally at a predetermined pressure level.

72. An apparatus according to claim 71, wherein said pressure regulation means is further defined as regulating the pressure of the gaseous sampling medium to substantially atmospheric pressure.

73. An apparatus according to claim 65, further including temperature sensing means for sensing a core temperature of the human or other mammal, said temperature sensing means being exposed to said sampling medium.

74. An apparatus according to claim 73, wherein said temperature sensing means is in said sampling chamber.

75. An apparatus according to claim 65, further including pressure sensing means for sensing a respiration rate of the human or other mammal, said pressure sensing means being in fluid communication with said sampling chamber.

76. An apparatus according to claim 75, wherein said pressure sensing means is in said sampling chamber.

77. A method of measuring a liquid fluid or gaseous fluid property indicative of the condition of an organ of the body of a human or other mammal in vivo, comprising the steps of:
(a) providing a flexible, elongated tonometric catheter tube having at least one lumen extending longitudinally therethrough with at least one sampling chamber on said catheter tube for receiving, containing, and discharging a gaseous sampling medium, said sampling chamber having a wall and being in fluid communication with the interior of said at least one lumen, said sampling chamber generally surrounding a portion of said catheter tube and being sealingly interconnected therewith, the wall of said sampling chamber being composed of a wall material that is selectively permeable to one or more liquid fluids or gaseous fluids of interest that are present in the organ, said wall material being substantially impermeable to other liquid fluids or gaseous fluids that are present in the organ, said sampling chamber defining an interior space between said sampling chamber and said catheter tube, said catheter tube being composed of a material that is substantially impermeable to the gaseous or liquid fluids of interest;

(b) providing a Raman sensor apparatus for sensing the level of at least one of said liquid fluids or gaseous fluids of interest with direct fluid communication between said sampling chamber and said Raman sensor apparatus via said at least one lumen of said catheter;

(c) introducing the catheter tube into the organ of interest so that said sampling chamber is disposed at a desired sampling site, said catheter tube extending to a position outside the body of the human or other mammal so that said at least one lumen provides fluid communication between said sampling chamber and the outside of the body of the human or other mammal and by which the direct fluid communication between said sampling chamber and said Raman sensor apparatus is provided;

(d) introducing a gaseous sampling medium into said catheter tube and into said interior space defined by said sampling chamber and said catheter tube;

(e) leaving said sampling chamber disposed at said sampling site for a length of time sufficient to allow said liquid fluid or gaseous fluids of interest that are present at said sampling site to diffuse across the wall of the sampling chamber into said gaseous sampling medium contained within said sampling chamber;

(f) withdrawing at least a portion of said gaseous sampling medium through said catheter tube to said Raman sensor apparatus by means of the direct fluid communication between said sampling chamber and said Raman sensor apparatus; and (g) analyzing the sample thus withdrawn using said Raman sensor means to determine the level present of said liquid fluid or gaseous fluid in said withdrawn gaseous sampling medium.

78. A method according to claim 77, wherein the step of providing a Raman sensor apparatus is further defined as providing Raman sensor apparatus of the in-stream type for measuring of said liquid fluids or gaseous fluids of interest.

79. A method according to claim 77, wherein the step of providing a Raman sensor apparatus is further defined as providing Raman sensor apparatus of the side-stream type for measuring said liquid fluids or gaseous fluids of interest.

80. A method according to claim 77, further including the step of providing a bio-filter device in said catheter tube between said walled sampling chamber and said Raman sensor apparatus and filtering said gaseous or liquid sampling medium through said bio-filter prior to analyzing said gaseous sampling medium using said Raman sensor apparatus in order to filter out undesirable contaminants.

81. A method according to claim 77, further including the step of measuring the pressure of said gaseous sampling medium.

82. A method according to claim 81, further including the step of regulating the pressure of said gaseous sampling medium generally at a predetermined pressure level.

83. A method according to claim 82, wherein the step of regulating the pressure to a predetermined Pressure level is further defined as regulating the pressure to substantially atmospheric pressure.

84. A method according to claim 77, further including the step of providing a temperature sensing means for sensing a core temperature of the human or other mammal, said temperature sensing means being exposed to said sampling medium.

85. A method according to claim 84, wherein the step of Providing a temperature sensing means is further defined as providing a temperature sensing means in said sampling chamber.

86. A method according to claim 77, further including the step of providing a pressure sensing means for sensing a respiration rate of the human or other mammal, said pressure sensing means being provided in fluid communication with said sampling chamber.

87. A method according to claim 86, wherein the step of providing a pressure sensing means is further defined as providing a pressure sensing means in said sampling chamber.

88. A method of measuring a liquid fluid or gaseous fluid property indicative of the condition of an organ of the body of a human or other mammal in vivo comprising the steps of:

(a) providing a flexible, elongated tonometric catheter tube having at least one lumen extending longitudinally therethrough with at least one sampling chamber on said catheter tube for receiving, containing, and discharging a gaseous sampling medium and being in fluid communication with the interior of said lumen, said sampling chamber being defined by a balloon member generally surrounding a portion of said catheter tube and being sealingly interconnected therewith, said balloon member having a wall, the wall of said balloon member being composed of a wall material that is selectively permeable to one or more liquid fluids or gaseous fluids of interest, said wall material being substantially impermeable to other liquid fluids or gaseous fluids, said balloon member defining an interior space between said sampling chamber and said catheter tube, said catheter tube being composed of a material that is substantially impermeable to the gaseous or liquid fluids of interest;

(b) providing an Raman sensor apparatus for sensing the level of at least one of said liquid fluids or gaseous fluids of interest with direct fluid communication between said sampling chamber and said Raman sensor apparatus via said at least one lumen of said catheter;

(c) introducing the catheter tube into the organ of interest so that said balloon member is disposed at a desired sampling site, said catheter tube extending to a position outside the body of the human or other mammal so that said lumen provides fluid communication between said balloon member and the outside of the body of the human or other mammal and by which the direct fluid communication between said sampling chamber and said Raman sensor apparatus is provided;

(d) introducing a gaseous sampling medium into said catheter tube and into said interior space defined by said balloon member and said catheter tube;

(e) leaving said sampling chamber disposed at said sampling site for a length of time sufficient to allow said liquid fluids or gaseous fluids of interest that are present at said sampling site to diffuse across the wall of the balloon member into said gaseous sampling medium contained within said balloon member;

(f) withdrawing at least a portion of said gaseous or liquid sampling medium through said catheter tube to said Raman sensor apparatus by means of the direct fluid communication between said sampling chamber and said Raman sensor apparatus; and (g) analyzing the sample thus withdrawn using said Raman sensor means to determine the level present of said liquid fluid or gaseous fluid in said withdrawn gaseous sampling medium.

89. A method according to claim 88, wherein the step of providing a Raman sensor apparatus is further defined as providing Raman sensor apparatus of the in-stream type for measuring of said liquid fluids or gaseous fluids of interest.

90. A method according to claim 88, wherein the step of providing a Raman sensor apparatus is further defined as providing Raman sensor apparatus of the side-stream type for measuring said liquid fluids or gaseous fluids of interest.

91. A method according to claim 88, further including the step of providing a bio-filter device in said catheter tube between said walled sampling chamber and said Raman sensor apparatus and filtering said gaseous or liquid sampling medium through said bio-filter prior to said analyzing said gaseous sampling medium using said Raman sensor apparatus in order to filter out undesirable contaminants.

92. A method according to claim 88, further including the step of measuring the pressure of said gaseous or liquid sampling medium.

93. A method according to claim 92, further including the step of regulating the pressure of said gaseous or liquid sampling medium generally at a predetermined pressure level.

94. A method according to claim 93, wherein the step of regulating the pressure to a predetermined pressure level is further defined as regulating the pressure to substantially atmospheric pressure.

95. A method according to claim 88, further including the step of providing a temperature sensing means for sensing a core temperature of the human or other mammal, said temperature sensing means being exposed to said sampling medium.

96. A method according to claim 95, wherein the step of providing a temperature sensing means is further defined as providing a temperature sensing means in said sampling chamber.

97. A method according to claim 88, further including the step of providing a pressure sensing means for sensing a respiration rate of the human or other mammal, said pressure sensing means being provided in fluid communication with said sampling chamber.

98. A method according to claim 97, wherein the step of providing a pressure sensing means is further defined as providing a pressure sensing means in said sampling chamber.

* * * * *